US012580043B2

(12) United States Patent
Park et al.

(10) Patent No.: US 12,580,043 B2
(45) Date of Patent: Mar. 17, 2026

(54) MOLECULE DESIGN WITH MULTI-OBJECTIVE OPTIMIZATION OF PARTIALLY ORDERED, MIXED-VARIABLE MOLECULAR PROPERTIES

(71) Applicant: Genentech, Inc., South San Francisco, CA (US)

(72) Inventors: Ji Won Park, Foster City, CA (US); Samuel Don Stanton, Brooklyn, NY (US); Andrew Martin Watkins, San Francisco, CA (US); Kyunghyun Cho, New York, NY (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 19/098,389

(22) Filed: Apr. 2, 2025

(65) Prior Publication Data

US 2025/0232834 A1    Jul. 17, 2025

Related U.S. Application Data

(63) Continuation of application No. PCT/US2023/075809, filed on Oct. 3, 2023.

(60) Provisional application No. 63/378,186, filed on Oct. 3, 2022, provisional application No. 63/385,609, filed on Nov. 30, 2022.

(51) Int. Cl.
| | |
|---|---|
| *G16B 15/30* | (2019.01) |
| *G06N 20/20* | (2019.01) |
| *G16B 40/20* | (2019.01) |
| *G16C 20/30* | (2019.01) |
| *G16C 20/50* | (2019.01) |
| *G16C 20/70* | (2019.01) |

(52) U.S. Cl.
CPC ............. *G16B 15/30* (2019.02); *G06N 20/20* (2019.01); *G16B 40/20* (2019.02); *G16C 20/30* (2019.02); *G16C 20/50* (2019.02); *G16C 20/70* (2019.02)

(58) Field of Classification Search
None
See application file for complete search history.

(56) References Cited

U.S. PATENT DOCUMENTS

2022/0348903 A1* 11/2022 Ranganathan ......... G16B 25/10

FOREIGN PATENT DOCUMENTS

| | | |
|---|---|---|
| WO | WO 2022/090579 A1 | 5/2022 |
| WO | WO 2022/167821 A1 | 8/2022 |

OTHER PUBLICATIONS

Shmilovich, Kirill, et al. "Hybrid computational-experimental data-driven design of self-assembling π-conjugated peptides." Digital Discovery 1.4 (2022): 448-462. (Year: 2022).*
International Searching Authority, International Search Report and Written Opinion, mailed Feb. 2, 2024, for International Patent Application No. PCT/US2024/075809.
Astudillo et al., 2021, "Bayesian optimization of function networks," Advances in Neural Information Processing Systems, 34:14463-14475.
Bellamy et al., 2022, "Batched Bayesian optimization for drug design in noisy environments," Journal of Chemical Information and Modeling.
Biswas et al., 2021, "Low-n protein engineering with data-efficient deep learning," Nature methods, 18(4):389-396.
Das et al., 2021, "Accelerated antimicrobial discovery via deep generative models and molecular dynamics simulations," Nature Biomedical Engineering, 5(6):613-623.
Daulton et al., 2020, "Differentiable expected hypervolume improvement for parallel multi-objective bayesian optimization," Advances in Neural Information Processing Systems, 33:9851-9864, 2020.
Daulton et al., 2021, "Parallel bayesian optimization of multiple noisy objectives with expected hypervolume improvement," Advances in Neural Information Processing Systems, 34:2187-2200.
Daulton et al., 2022, "Bayesian optimization over discrete and mixed spaces via probabilistic reparameterization," In ICML2022 Workshop on Adaptive Experimental Design and Active Learning in the Real World.
Pyzer-Knapp, 2018, "Bayesian optimization for accelerated drug discovery," IBM Journal of Research and Development, 62(6):2-1.
Eggers., 2015, "On statistical methods for zero-inflated models."
Emmerich et al., 2011, "Hypervolume-based expected improvement: Monotonicity properties and exact computation," In 2011 IEEE Congress of Evolutionary Computation (CEC), pp. 2147-2154. IEEE.
Emmerich, 2005, "Single-and multi-objective evolutionary design optimization assisted by gaussian random field metamodels." PhD thesis, Dortmund, Univ., Diss.
Frazier, 2018, "A tutorial on bayesian optimization. arXiv preprint," arXiv: 1807.02811.
Gardner et al., 2014, "Bayesian optimization with inequality constraints," In ICML, vol. 2014, pp. 937-945.

(Continued)

*Primary Examiner* — Olivia M. Wise
*Assistant Examiner* — Jonathan Edward Hayes
(74) *Attorney, Agent, or Firm* — Jones Day

(57)    ABSTRACT

One or more property computational models may be applied to determine a first probability of a molecule design exhibiting a first property and a second probability of the molecule design exhibiting a second property. A plurality of samples in which each sample includes a first value of the first property and a second value of the second property exhibited by the molecule design may be determined based on the output of the property computational models. A set of samples in which the first value of the first property satisfies a criterion may be identified. A utility metric corresponding to an expected improvement of the first property and the second property of the molecule design over that of baseline molecule designs may be determined based on the set of samples. One or more molecule designs may be identified as candidates for synthesis based on the corresponding utility metrics.

26 Claims, 16 Drawing Sheets

(56) References Cited

OTHER PUBLICATIONS

Gelbart et al., 2014, "Bayesian optimization with unknown constraints," arXiv preprint arXiv:1403.5607.

Ginsbourger et al., 2010, "Kriging is well-suited to parallelize optimization," In Computational intelligence in expensive optimization problems, pp. 131-162. Springer.

Gligorijevic et al., 2021, "Function-guided protein design by deep manifold sampling," bioRxiv.

Grün et al., 2014, "Validation of noise models for single-cell transcriptomics," Nature methods, 11(6):637-640.

Hernández-Lobato et al., 2016, "A general framework for constrained bayesian optimization using information-based search."

Jain et al., 2017, "Biophysical properties of the clinical-stage antibody landscape," Proceedings of the National Academy of Sciences, 114(5):944-949.

Jarasch et al., 2015, "Developability assessment during the selection of novel therapeutic antibodies," Journal of pharmaceutical sciences, 104(6):1885-1898.

Jones et al., 1998, "Efficient global optimization of expensive black-box functions," Journal of Global optimization, 13(4):455-492.

Letham et al., 2019, "Constrained bayesian optimization with noisy experiments," Bayesian Analysis, 14(2):495-519.

Liang et al., 2021, "Scalable bayesian optimization accelerates process optimization of penicillin production," In NeurIPS 2021 AI for Science Workshop.

Malkomes et al., 2021, "Beyond the pareto efficient frontier: Constraint active search for multiobjective experimental design," In International Conference on Machine Learning, pp. 7423-7434. PMLR.

Mayr et al., 2009, "Novel trends in high-throughput screening," Current opinion in pharmacology, 9(5):580-588.

Mockus, 1975, "On bayesian methods for seeking the extremum," In Optimization techniques IFIP technical conference, pp. 400-404. Springer.

Park et al., 2022, "Propertydag: Multi-objective bayesian optimization of partially ordered, mixed-variable properties for biological sequence design," arXiv.

Rasmussen et al., 2005, "Gaussian processes for machine learning (adaptive computation and machine learning)."

Shahriari et al., 2015, "Taking the human out of the loop: A review of bayesian optimization," Proceedings of the IEEE, 104(1):148-175.

Sinai et al., 2020, "A primer on model-guided exploration of fitness landscapes for biological sequence design," arXiv preprint arXiv:2010.10614.

Stanton et al., 2022, "Accelerating bayesian optimization for biological sequence design with denoising autoencoders," arXiv preprint arXiv:2203.12742, 2022.

Wada et al., 2019, "Bayesian optimization for multi-objective optimization and multi-point search," arXiv preprint arXiv:1905.02370.

Wu et al. 2016 "The parallel knowledge gradient method for batch bayesian optimization," Advances in neural information processing systems, 29, 2016.

Yang et al., 2019, "A multi-point mechanism of expected hypervolume improvement for parallel multi-objective bayesian global optimization," In Proceedings of the Genetic and Evolutionary Computation Conference, pp. 656-663.

* cited by examiner

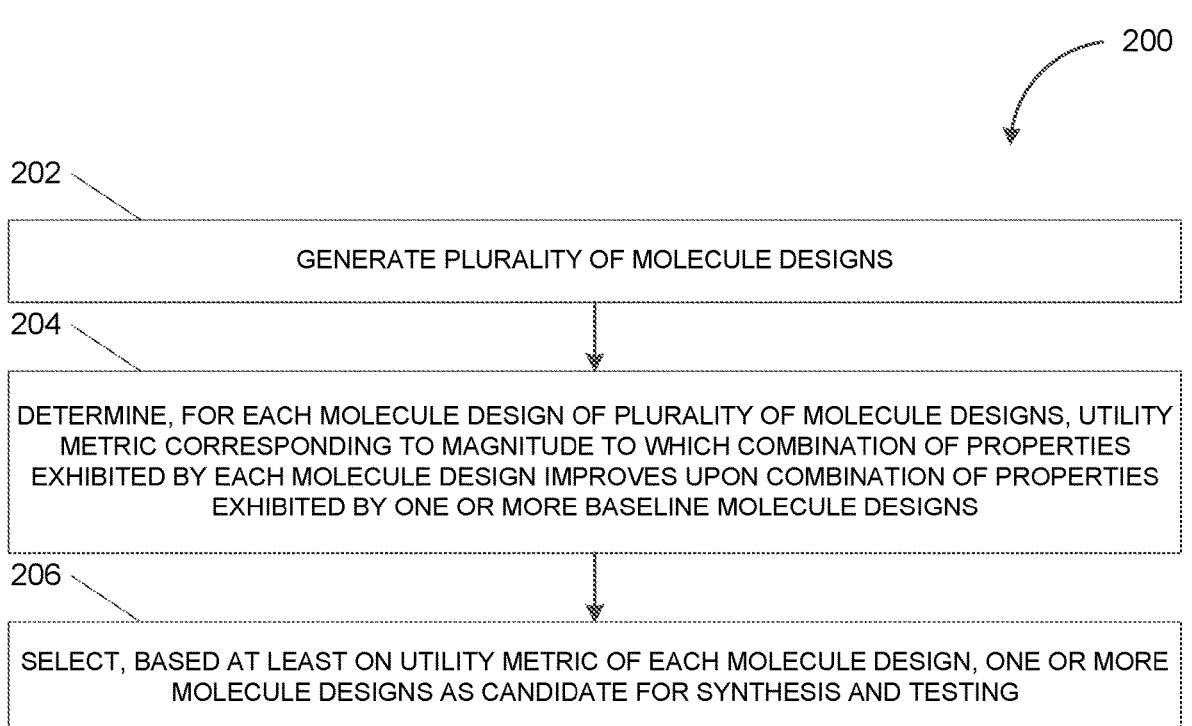

200

202

GENERATE PLURALITY OF MOLECULE DESIGNS

204

DETERMINE, FOR EACH MOLECULE DESIGN OF PLURALITY OF MOLECULE DESIGNS, UTILITY METRIC CORRESPONDING TO MAGNITUDE TO WHICH COMBINATION OF PROPERTIES EXHIBITED BY EACH MOLECULE DESIGN IMPROVES UPON COMBINATION OF PROPERTIES EXHIBITED BY ONE OR MORE BASELINE MOLECULE DESIGNS

206

SELECT, BASED AT LEAST ON UTILITY METRIC OF EACH MOLECULE DESIGN, ONE OR MORE MOLECULE DESIGNS AS CANDIDATE FOR SYNTHESIS AND TESTING

FIG. 2A

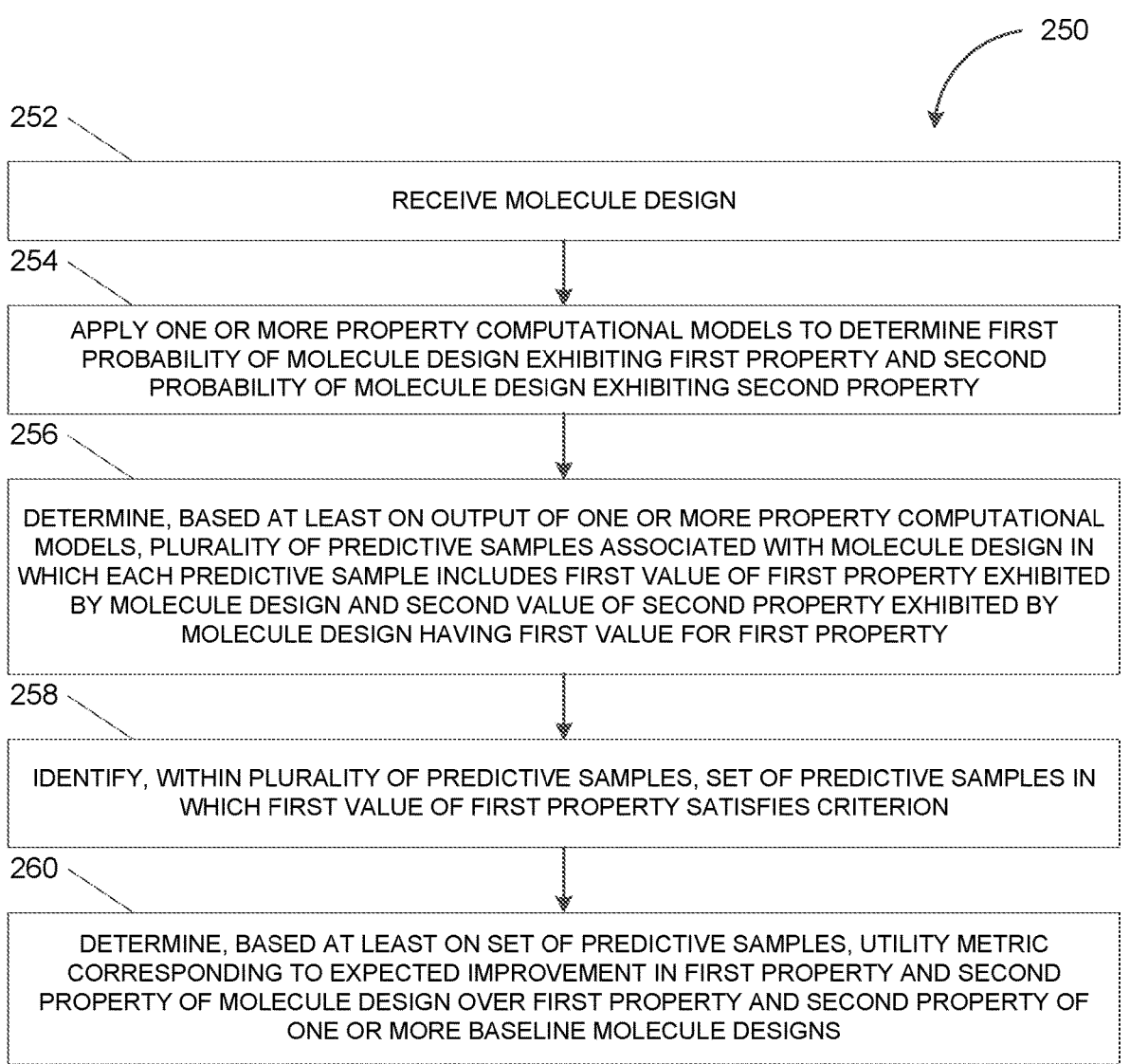

250

252

RECEIVE MOLECULE DESIGN

254

APPLY ONE OR MORE PROPERTY COMPUTATIONAL MODELS TO DETERMINE FIRST
PROBABILITY OF MOLECULE DESIGN EXHIBITING FIRST PROPERTY AND SECOND
PROBABILITY OF MOLECULE DESIGN EXHIBITING SECOND PROPERTY

256

DETERMINE, BASED AT LEAST ON OUTPUT OF ONE OR MORE PROPERTY COMPUTATIONAL
MODELS, PLURALITY OF PREDICTIVE SAMPLES ASSOCIATED WITH MOLECULE DESIGN IN
WHICH EACH PREDICTIVE SAMPLE INCLUDES FIRST VALUE OF FIRST PROPERTY EXHIBITED
BY MOLECULE DESIGN AND SECOND VALUE OF SECOND PROPERTY EXHIBITED BY
MOLECULE DESIGN HAVING FIRST VALUE FOR FIRST PROPERTY

258

IDENTIFY, WITHIN PLURALITY OF PREDICTIVE SAMPLES, SET OF PREDICTIVE SAMPLES IN
WHICH FIRST VALUE OF FIRST PROPERTY SATISFIES CRITERION

260

DETERMINE, BASED AT LEAST ON SET OF PREDICTIVE SAMPLES, UTILITY METRIC
CORRESPONDING TO EXPECTED IMPROVEMENT IN FIRST PROPERTY AND SECOND
PROPERTY OF MOLECULE DESIGN OVER FIRST PROPERTY AND SECOND PROPERTY OF
ONE OR MORE BASELINE MOLECULE DESIGNS

FIG. 2B (a) Default (b) PropertyDAG resampling

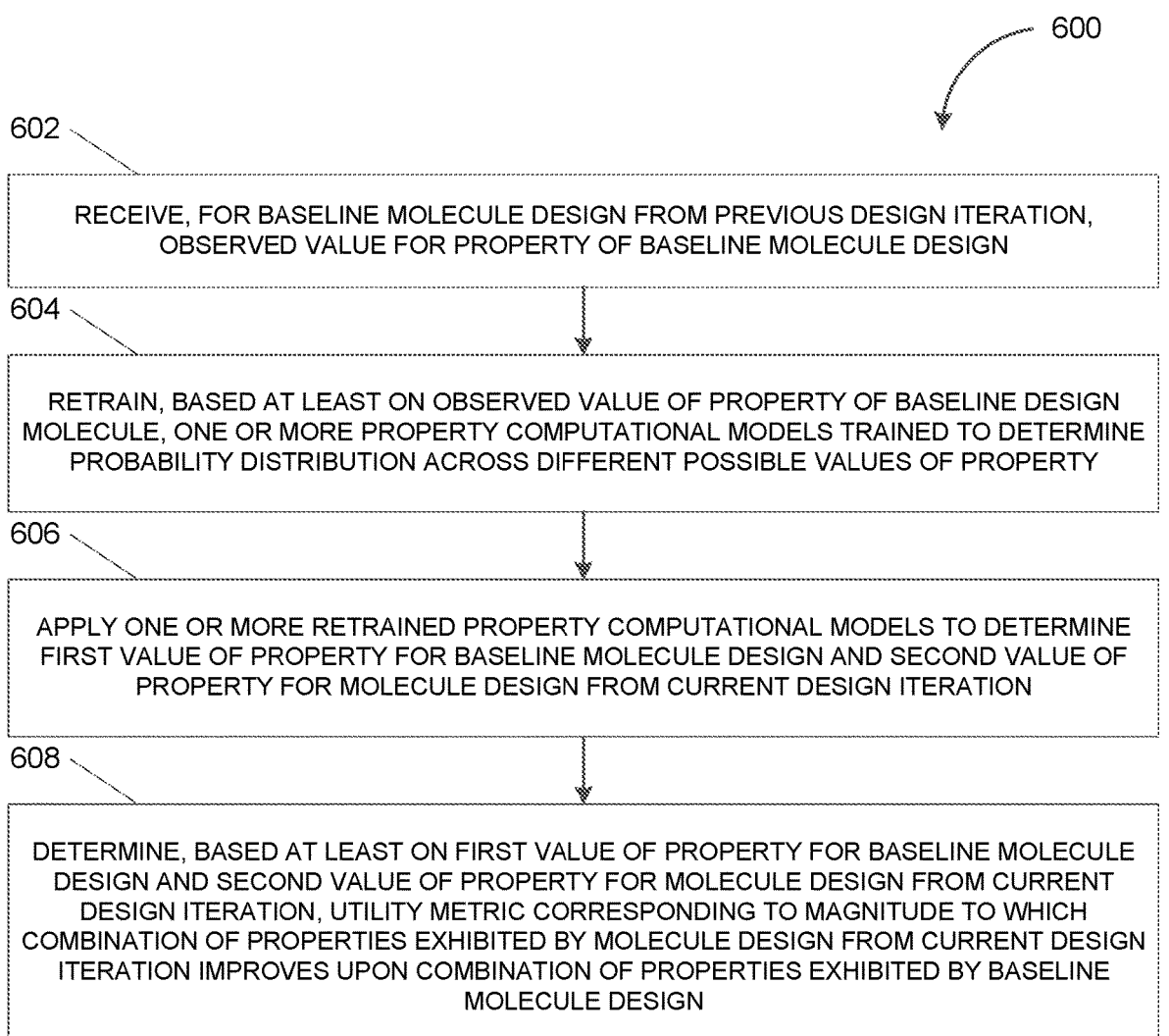

600

602
RECEIVE, FOR BASELINE MOLECULE DESIGN FROM PREVIOUS DESIGN ITERATION, OBSERVED VALUE FOR PROPERTY OF BASELINE MOLECULE DESIGN

604
RETRAIN, BASED AT LEAST ON OBSERVED VALUE OF PROPERTY OF BASELINE DESIGN MOLECULE, ONE OR MORE PROPERTY COMPUTATIONAL MODELS TRAINED TO DETERMINE PROBABILITY DISTRIBUTION ACROSS DIFFERENT POSSIBLE VALUES OF PROPERTY

606
APPLY ONE OR MORE RETRAINED PROPERTY COMPUTATIONAL MODELS TO DETERMINE FIRST VALUE OF PROPERTY FOR BASELINE MOLECULE DESIGN AND SECOND VALUE OF PROPERTY FOR MOLECULE DESIGN FROM CURRENT DESIGN ITERATION

608
DETERMINE, BASED AT LEAST ON FIRST VALUE OF PROPERTY FOR BASELINE MOLECULE DESIGN AND SECOND VALUE OF PROPERTY FOR MOLECULE DESIGN FROM CURRENT DESIGN ITERATION, UTILITY METRIC CORRESPONDING TO MAGNITUDE TO WHICH COMBINATION OF PROPERTIES EXHIBITED BY MOLECULE DESIGN FROM CURRENT DESIGN ITERATION IMPROVES UPON COMBINATION OF PROPERTIES EXHIBITED BY BASELINE MOLECULE DESIGN

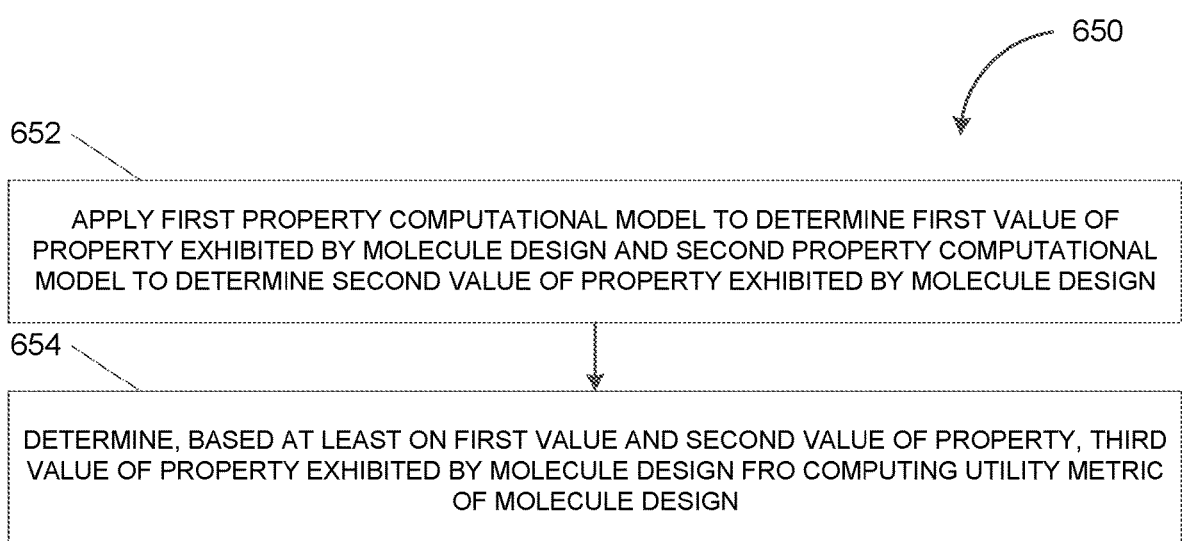

APPLY FIRST PROPERTY COMPUTATIONAL MODEL TO DETERMINE FIRST VALUE OF PROPERTY EXHIBITED BY MOLECULE DESIGN AND SECOND PROPERTY COMPUTATIONAL MODEL TO DETERMINE SECOND VALUE OF PROPERTY EXHIBITED BY MOLECULE DESIGN

654

DETERMINE, BASED AT LEAST ON FIRST VALUE AND SECOND VALUE OF PROPERTY, THIRD VALUE OF PROPERTY EXHIBITED BY MOLECULE DESIGN FRO COMPUTING UTILITY METRIC OF MOLECULE DESIGN

FIG. 6B (A)

(a) Penicillin production

(B)

(b) Branin-Currin toy problem

MOLECULE DESIGN WITH MULTI-OBJECTIVE OPTIMIZATION OF PARTIALLY ORDERED, MIXED-VARIABLE MOLECULAR PROPERTIES

CROSS REFERENCE TO RELATED APPLICATIONS

This application is a bypass continuation of International Patent Application No. PCT/US2023/075809 entitled "MOLECULE DESIGN WITH MULTI-OBJECTIVE OPTIMIZATION OF PARTIALLY ORDERED, MIXED-VARIABLE MOLECULAR PROPERTIES" and filed on Oct. 3, 2023, which claims priority to U.S. Provisional Application No. 63/378,186, entitled "MULTI-OBJECTIVE ACTIVE LEARNING FOR MOLECULE DESIGN" and filed on Oct. 3, 2022, and U.S. Provisional Application No. 63/385,609, entitled "MULTI-OBJECTIVE ACTIVE LEARNING FOR MOLECULE DESIGN" and filed on Nov. 30, 2022, the disclosures of each of which are incorporated herein by reference in their entirety.

TECHNICAL FIELD

The subject matter described herein relates generally to molecular design and more specifically to a multi-objective active learning technique for molecule design.

INTRODUCTION

A molecule is a group of two more atoms held together by chemical bonds. Molecules form the smallest identifiable unit into which a pure substance can be divided while still retaining the composition and chemical properties of that substance. One example of a molecule is a protein molecule while examples of non-protein molecules include small molecules, ions, nucleic acids, polysaccharides, glycolipids, and/or the like. The function and properties of a molecule may be contingent upon its three-dimensional structure. For example, proteins are responsible for many essential cellular functions including, for example, enzymatic reactions, transport of molecules, regulation and execution of a number of biological pathways, cell growth, proliferation, nutrient uptake, morphology, motility, intercellular communication, and/or the like.

A protein structure may include one or more polypeptides, which are chains of amino acid residues linked together by peptide bonds. The sequence of amino acid residues in the polypeptide chains forming the protein structure determines the protein's three-dimensional structure (e.g., the protein's tertiary structure). Moreover, the sequence of amino acids in the polypeptide chains forming the protein determines the protein's underlying functions. As such, one objective of protein design may include constructing one or more sequences of amino acid residues that exhibit a variety of desirable properties. For example, in the case of large molecule drug discovery, de novo protein design will often seek to identify sequences of amino acid residues (e.g., antibodies and/or the like) capable of binding to a target antigen (e.g., such as a viral antigen, a tumor antigen, and/or the like) including by adopting a three-dimensional structure that complements the three-dimensional structure of the target antigen.

SUMMARY

Systems, methods, and articles of manufacture, including computer program products, are provided for molecule design with multi-objective active learning. In one aspect, there is provided a system for molecule design with multi-objective active learning. The system may include at least one data processor and at least one memory. The at least one memory may store instructions, which causes operations when executed by the at least one data processor. The operations may include: applying, to a first molecule design, one or more property computational models trained to determine a first probability of the first molecule design exhibiting a first property and second probability of the first molecule design exhibiting a second property; determining, based at least on an output of the one or more property computational models, a first plurality of samples associated with the first molecule design, each sample of the first plurality of samples including a first value of the first property exhibited by the first molecule design and a second value of the second property exhibited by the first molecule design having the first value for the first property; identifying, within the first plurality of samples, a first set of samples in which the first value of the first property satisfies a first criterion; determining, based at least on the first set of samples, a first utility metric corresponding to a first expected improvement in the first property and the second property of the first molecule design over the first property and the second property of one or more baseline molecule designs; and identifying, based at least on the first utility metric of the first molecule design, the first molecule design as a candidate for synthesis.

In another aspect, there is provided a method for molecule design with multi-objective optimization. The method may include: applying, to a first molecule design, one or more property computational models trained to determine a first probability of the first molecule design exhibiting a first property and second probability of the first molecule design exhibiting a second property; determining, based at least on an output of the one or more property computational models, a first plurality of samples associated with the first molecule design, each sample of the first plurality of samples including a first value of the first property exhibited by the first molecule design and a second value of the second property exhibited by the first molecule design having the first value for the first property; identifying, within the first plurality of samples, a first set of samples in which the first value of the first property satisfies a first criterion; determining, based at least on the first set of samples, a first utility metric corresponding to a first expected improvement in the first property and the second property of the first molecule design over the first property and the second property of one or more baseline molecule designs; and identifying, based at least on the first utility metric of the first molecule design, the first molecule design as a candidate for synthesis.

In another aspect, there is provided a non-transitory computer program product for molecule design with multi-objective active learning. The non-transitory computer program product may store instructions that cause operations when performed by at least one data processor. The operations may include: applying, to a first molecule design, one or more property computational models trained to determine a first probability of the first molecule design exhibiting a first property and second probability of the first molecule design exhibiting a second property; determining, based at least on an output of the one or more property computational models, a first plurality of samples associated with the first molecule design, each sample of the first plurality of samples including a first value of the first property exhibited by the first molecule design and a second value of the second property exhibited by the first molecule design having the first value for the first property; identifying, within the first plurality of samples, a first set of samples in which the first value of the first property satisfies a first criterion; determining, based at least on the first set of samples, a first utility metric corresponding to a first expected improvement in the first property and the second property of the first molecule design over the first property and the second property of one or more baseline molecule designs; and identifying, based at least on the first utility metric of the first molecule design, the first molecule design as a candidate for synthesis.

In some variations of the methods, systems, and non-transitory computer readable media, one or more of the following features can optionally be included in any feasible combination.

In some variations, the first utility metric may be determined by applying an expected hypervolume improvement (EHVI), a noisy expected hypervolume improvement (NEHVI), a Pareto efficient global optimization (ParEGO), a max-value entropy search method (MESMO), or a joint entropy search (JES).

In some variations, the one or more property computational models may be retrained based at least on one or more in vitro measurements and/or in vivo characterizations associated with the one or more baseline molecule designs. The one or more retrained property computational models may be applied to determine the first property and the second property of the one or more baseline molecules.

In some variations, a second set of samples in which the first value of the first property fails to satisfy the first criterion may be identified within the first plurality of samples. The first utility metric may be determined to include a first contribution from the first set of samples and exclude a second contribution from the second set of samples.

In some variations, the one or more property computational models trained to determine a third probability of the first molecule design exhibiting a third property may be applied to the first molecule design. The first plurality of samples may be determined, based at least on the output of the one or more property computational models, to further include, as a part of each sample, a third value of the third property exhibited by the first molecule design. The first set of samples may be further identified based on the first value of the first property satisfying the first criterion and the second value of the second property satisfying a second criterion. The first utility metric may be determined, based at least on the first set of samples, to further correspond to the first expected improvement in the first property, the second property, and the third property of the first molecule design over the first property, the second property, and the third property of the one or more baseline molecules.

In some variations, the first property and the second property may occupy a same level a hierarchy above the third property such that the first molecule design is required to satisfy the first criterion associated with the first property as well as the second criterion associated with the second property before the first molecule design is evaluated for the third property.

In some variations, the first property and the second property may occupy different levels of a hierarchy above the third property such that the first molecule design is required to satisfy the first criterion associated with the first property before the first molecule design is evaluated for the second property. The first molecule design may be further required to satisfy the second criterion associated the second property before the first molecule design is evaluated for the third property.

In some variations, the one or more property computational models may include a first property computational model trained to determine the first probability of the first molecule design exhibiting the first property.

In some variations, the first property computational model may include a first probabilistic binary classifier trained to output a first value when the first probability satisfies a second threshold and a second value when the first probability fails to satisfy the second threshold. The first property computational model may further include a first probabilistic regressor trained to determine the first value of the first property exhibited by the first molecule design.

In some variations, the one or more property computational models may further include a second property computational model trained to determine the second probability of the first molecule exhibiting the second property.

In some variations, the second property computational model may include a second binary classifier trained to output a first value when the second probability satisfies a second threshold and a second value when the second probability fails to satisfy the second threshold. The second property computational model may further include a second regressor trained to determine the second value of the second property exhibited by the first molecule design.

In some variations, the one or more property computational models may include an ensemble of property computational models. The first probability of the first molecule design exhibiting the first property and/or the second probability of the first molecule design exhibiting the second property may be determined based at least on an output of the ensemble of property computational models.

In some variations, the one or more property computational may be applied to a second molecule design to determine a third probability of the second molecule design exhibiting the first property and a fourth probability of the second molecule design exhibiting the second property. A second plurality of samples associated with the second molecule design may be determined based at least on the output of the one or more property computational models. Each sample of the second plurality of samples may include a third value of the first property exhibited by the second molecule design and a fourth value of the second property exhibited the second molecule design. A second set of samples in which the third value of the first property satisfies the first criterion may be identified within the second plurality of samples. A second utility metric corresponding to a second expected improvement in the first property and the second property of the second molecule design over the first property and the second property of the one or more baseline molecule designs may be determined based at least on the second set of samples. The second molecule design may be identified, based at least on the second utility metric of the second molecule design, as another candidate for synthesis.

In some variations, the one or more baseline molecule designs may be updated to include the first molecule design such that the second expected improvement includes an expected improvement in the first property and the second property of the second molecule design over the first property and the second property of the first molecule design.

In some variations, the one or more baseline molecule designs may be updated to include one or more in vivo measurements and/or in vivo characterizations of the first property and/or the second property exhibited by the first molecule design.

In some variations, the one or more baseline molecule designs may be updated to include an average of the first plurality of samples associated with the first molecule design.

In some variations, each of the first probability of the first molecule design exhibiting the first property and/or the second probability of the first molecule design exhibiting the second property may include (i) a first probability distribution across a first value indicative of a corresponding property being present in the first molecule design and a second value indicative of the corresponding property being absent from the first molecule design, and (ii) a second probability distribution across a range of possible values indicative of a magnitude of the corresponding property exhibited by the first molecule design.

In some variations, the first molecule design may be identified as the candidate for synthesis based at least on the first utility metric of the first molecule design satisfying one or more thresholds.

In some variations, an N quantity of molecule designs having a highest utility metric may be selected as candidates for synthesis. The first molecule design may be identified as the candidate for synthesis based at least on the first molecule design being one of the N quantity of molecule designs having the highest utility metric.

In some variations, the first molecule design may be identified as the candidate for synthesis based at least on a presence or an absence of one or more specific amino acid residues in the first molecule design.

In some variations, the first plurality of samples may include a distribution of the second value of the second property exhibited by the first molecule design across the first value of the first property exhibited by the first molecule design.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to the design of biological sequences such as protein molecules, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 2A depicts a flowchart illustrating an example of a process for molecule design with multi-objective optimization of partially ordered, mixed-variable properties, in accordance with some example embodiments;

FIG. 2B depicts a flowchart illustrating another example of a process for molecule design with multi-objective optimization of partially ordered, mixed-variable properties, in accordance with some example embodiments;

FIG. 6A depicts a flowchart illustrating an example of a process for determining the probability of a molecule design exhibiting a property, in accordance with some example embodiments;

FIG. 6B depicts a flowchart illustrating another example of a process for determining the probability of a molecule design exhibiting a property, in accordance with some example embodiments;

When practical, similar reference numbers denote similar structures, features, or elements.

DETAILED DESCRIPTION

Figure 1:
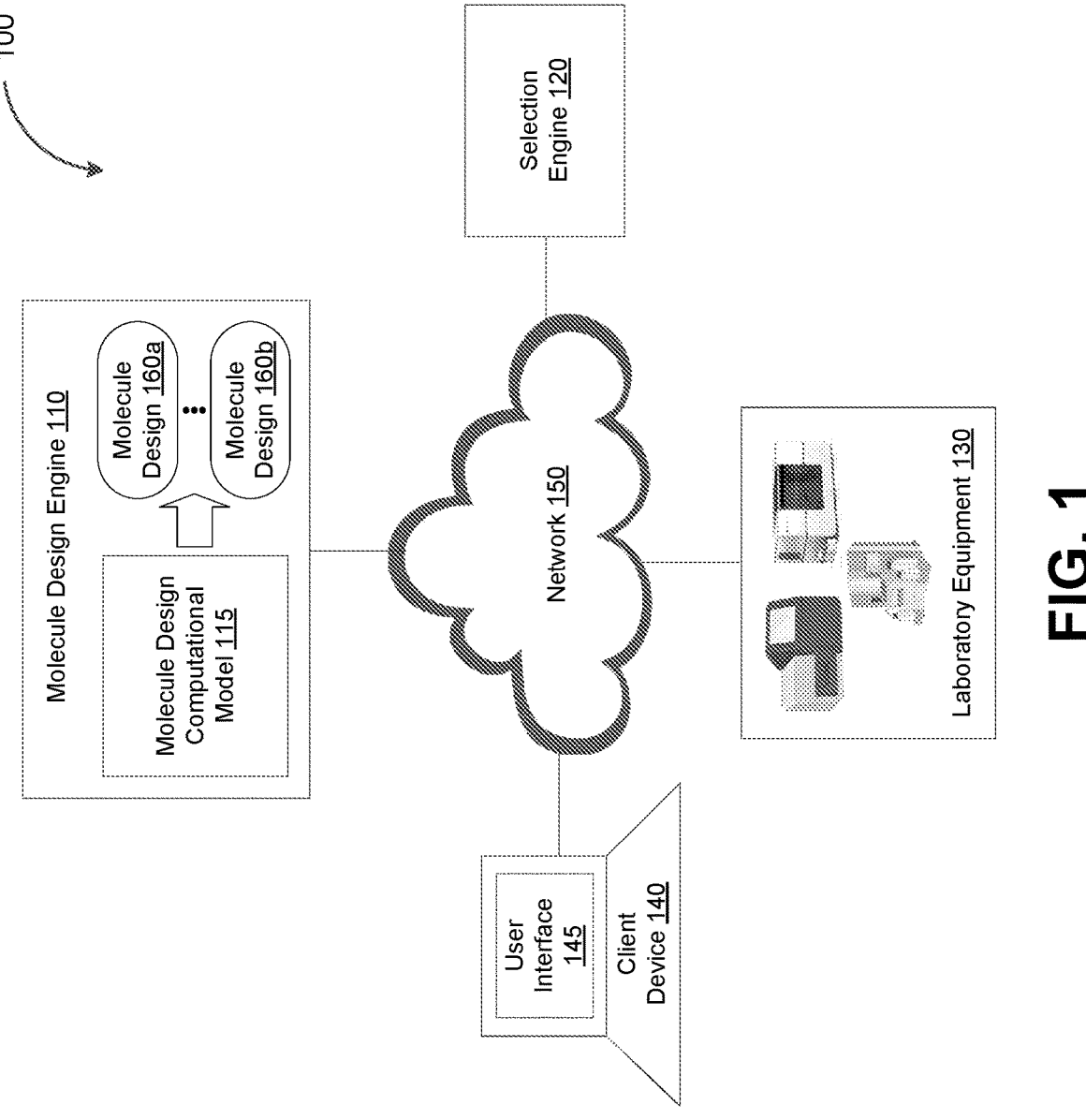
FIG. 1 depicts a system diagram illustrating an example of a molecule design system, in accordance with some example embodiments.

Designing a molecule, including biological sequences such as proteins or non-biological small molecules, entails searching over vast combinatorial design spaces. For example, de novo protein design aims to identify protein sequences (e.g., sequences of amino acid residues) that exhibit a litany of desirable properties, such as expression, binding affinity towards another molecule (e.g., a viral antigen, a tumor antigen, and/or the like), lack of non-specificity, stability, lack of immunogenicity, human-ness, lack of self-association, and/or the like. De novo protein design is a particularly challenging and resource intensive task at least because the combinatorial search space of every possible permutation of amino acid residues that can form a protein structure is vast but sparsely populated by sequences of amino acid residues that correspond to actually functional proteins. That is, the vast majority of protein sequences in the combinatorial search space will not exhibit any function at all, let alone a combination of the aforementioned desired properties. A search of this vast combinatorial search space becomes even more computationally intractable when considering candidate protein sequences of variable lengths (e.g., candidate protein sequences formed by different quantities of amino acid residues). Thus, a brute force approach that indiscriminately examines every possible sequence of amino acid residues to identify sequences that exhibit a desired property, even when performed in silico, is too computationally expensive to be a feasible solution.

In some example embodiments, instead of exploring a vast combinatorial space that is sparsely populated by functional molecules, a molecules design engine may generate one or more molecule designs including, for example, protein molecules, small molecules, ions, nucleic acids, polysaccharides, glycolipids, and/or the like, by sampling a data distribution associated with various known molecules. For example, the molecule design engine may include a molecule design computation model that is trained using known molecules including, for example, molecules known to exhibit certain functions and molecules without any known functions. In doing so, the molecule design computation model may learn a data distribution corresponding to a reduced dimension representation of the composition and/or structure of various known molecules. In the case of de novo protein design, for example, this data distribution may correspond to a reduced dimension representation of the sequences of amino acid residues forming various known protein sequences. In some cases, the data distribution may occupy a topological space (e.g., a manifold) occupied by the known molecules that describes the relationships that exist therebetween. Whereas the high dimensionality of the data associated with the known molecules tends to obscure the relationships between populations of molecules having compositional and/or structural similarities, the data distribution learned by the molecule design computation model may occupy a lower dimensional space in which one or more populations of molecules with compositional and/or structural similarities may form identifiable clusters.

Nevertheless, while computational molecular design models, including the aforementioned molecule design computation model, are capable of accelerating the initial molecular design process, limited wet lab resources still impose a bottleneck on the rate at which candidate molecular designs can undergo in vitro and in vivo assessment. In a typical drug development pipeline, a molecule design must be validated in vitro and undergo multiple rounds of optimization before the molecule design can proceed to preclinical development and clinical trials, where the performance of the molecule is tested in vivo. While a computational molecular design model, such as the aforementioned molecule design computation model, may be capable of generating a large quantity of molecule designs (e.g., in the order of millions of molecule designs), limited wet lab resources preclude the synthesis and in vitro assessment of every molecule design. Instead, a subset of molecule designs generated by the molecule design computation model may be selected for in vitro and/or in vivo assessment.

An indiscriminate selection of molecule designs for in vitro and/or in vivo assessment may increase the likelihood that those with poor molecular properties, such as suboptimal pharmacological and physiochemical properties that increase the likelihood of failure during subsequent preclinical development and clinical trials, are selected while better candidates are overlooked. In particular, in some cases, molecule designs may be generated and assessed over successive design iterations, with each design iteration (or design round) including the generating of one or more new molecule designs to improve upon those from one or more previous design iterations. Thus, the molecule designs that are selected for in vitro and/or in vivo assessment during a current design iteration should exhibit better molecular properties than those from previous design iterations. Accordingly, as described in more detail below, a selection engine may perform multi-objective optimization across a set of partially ordered, mixed variable molecular properties when selecting computationally generated molecule designs for further in vitro and/or in vivo assessment. Doing so may increase the likelihood that better molecule designs, such as those exhibiting better molecular properties than molecule designs from previous design iterations, are selected for in vitro and/or in vivo assessment.

In some example embodiments, the selection engine may perform multi-objective Bayesian optimization (BO), which leverages one or more probabilistic surrogate model and a utility function, to trade off exploration (evaluating highly uncertain molecule designs) and exploitation (evaluating molecule designs believed to increase or maximize the objectives) in a principled manner. For example, the selection engine may apply one or more property computational models trained to determine a first probability of a first molecule design generated by the molecule design computation model exhibiting a first property. Moreover, the selection engine may apply the one or more property computational models to determine a second probability of the first molecule design exhibiting a second property. In this context, the one or more property computational models may serve as an in silico surrogate for in vitro and/or in vivo evaluations, which are too resource intensive to apply to every molecule design generated by the molecule design computation model.

In some example embodiments, the one or more property computational models may be implemented as one or more zero-inflated probabilistic surrogate models, each of which including a probabilistic binary classifier and a probabilistic regressor model. Accordingly, in some cases, the output of the one or more property computational models may include a first plurality of predictive samples associated with the first molecule design or a predictive sample associated with the first molecule design. Each predictive sample associated with the first molecule design may include a first value of the first property exhibited by the first molecule design as well as a second value of the second property exhibited by the first molecule design having the first value of the first property. In some cases, multiple property computational models may be applied to generate the first plurality of predictive samples in order to account for the uncertainty in the output of each property computational model. Uncertainty in this context may refer to the level of confidence that the output of a property computational model, such as the value of a property predicted by the property computational model for a molecule design, is accurate. For example, in some cases, multiple property computational model(s) may be applied to determine the first value of the first property exhibited by the first molecule design while multiple property computational model(s) may also be applied to determine the second value of the second property exhibited by the first molecule design. Accordingly, a first predictive sample may include outputs from different property computational models than the property computational model(s) used to generate a second predictive sample. In some cases, the first plurality of samples associated with the first molecule design may form a first distribution of the second value of the second property exhibited by the first molecule design across the first value of the first property exhibited by the first molecule design. In the case of antibody design, the output of the one or more property computational models may include, for example, the distribution of the level of binding affinity exhibited by the first molecule design across the levels of expression exhibited by the first molecule design. That is, in the case of antibody design, the output of the one or more property computational models may include a predictive sample or multiple predictive samples, each of which includes an expression level of the first molecule design and a corresponding binding affinity of the first molecule design.

In some example embodiments, the selection engine may determine a first utility metric indicative of a first magnitude to which the first molecule design improves upon one or more baseline molecules designs with respect to the first property and the second property. For example, in the case of antibody design, the first utility metric of the first molecule design may be indicative of the magnitude to which the first molecule design improves upon the expression level as well as the binding affinity of the baseline molecule designs. Moreover, in some cases, the selection engine may select, based at least on the first utility metric of the first molecule design, the first molecule design as a candidate for synthesis and testing. In doing so, the selection engine may ensure that the first molecule design is selected as a candidate for synthesis and testing is a so-called joint positive molecule design, which refers to a molecule design that meets specific criteria with respect to the first property as well as the second property. As described in more detail below, the selection engine may perform multi-objective optimization in order to select the aforementioned joint positive molecule design. It should be appreciated that a joint positive molecule design is not necessarily a molecule design having the best value in every molecular property (e.g., highest expression and highest binding affinity) at least because such a molecule design may not exist at all. Instead, multi-objective optimization (MOO) in this context may include identifying a joint positive molecule design exhibiting a first value of a first property that cannot be improved without worsening a second value of a second property.

In some example embodiments, the selection engine may apply an active learning approach in which the first molecule design becomes one of the baseline molecule designs during subsequent design iterations. For example, the selection engine may determine to select a second molecule design generated by the molecule design computation model as the next candidate for synthesis based at least on a second utility metric indicative of a second magnitude to which the second molecule design improves upon the first property and the second property of the baseline molecule designs including the first molecule design. The respective values of the first property and the second property exhibited by the first molecule design may be determined based on the output of the one or more property computational models. Alternatively and/or additionally, the respective values of the first property and the second property exhibited by the first molecule may be determined based on one or more in vitro measurements or in vivo characterizations associated with the first molecule design. In some cases, to account for the noise (e.g., measurement errors associated with the laboratory equipment 130) that may be present in the one or more in vitro measurements or in vivo characterizations associated with the first molecule design, the respective values of the first property and the second property exhibited by the first molecule design may be determined based on the output of the one or more property computational models after the one or more property computational models have been updated, for example, by being retrained based on the one or more in vitro measurements or in vivo characterizations associated with the first molecule design.

In some example embodiments, the selection engine may impose a partial ordering to prioritize, for example, the first property over the second property, when determining the first utility metric associated with the first molecule design. As noted, the first utility metric associated with the first molecule design may be indicative of the first magnitude to which the first property and the second property of the first molecule design improve upon the first property and the second property of the one or more baseline molecules. In some cases, a partial ordering of the first property and the second property may require the first property of the first molecule design to satisfy a first criteria before the first molecule design is assessed to determine whether the second property of the first molecule design satisfies a second criteria. In the context of antibody design, for example, the selection engine may require that the expression level of the first molecule design to satisfy one or more criteria before the first molecule design is evaluated for its binding affinity to a target antigen in order to reflect an experimental and/or biological dependency in which the first molecule design may be required to reach a certain expression level before a sufficient quantity of the first molecule design can be synthesized and assayed for other properties such as binding affinity to the target antigen. Accordingly, to determine the first utility metric associated with the first molecule design while imposing the partial ordering to prioritize the first property over the second property, the selection engine may include contributions from a first sample in the first distribution where the first value of the first property satisfies the one or more criteria while excluding contributions from a second sample in the first distribution where the first value of the first property fails to satisfy the one or more criteria. In doing so, the first utility metric associated with the first molecule design may be indicative of the first magnitude to which the first property and the second property of the first molecule design improves upon the first property and the second property of the one or more baseline molecules designs where the first property of the first molecule design satisfies the one or more criteria.

In some example embodiments, the selection engine may further evaluate a third property of the first molecule design when selecting the first molecule design as a candidate for synthesis as well as in vitro measurements and/or in vivo characterizations. For example, the selection engine may apply the one or more property computational models to determine a third probability of the first molecule design exhibiting the third property. In this case, each predictive sample of the first plurality of predictive samples output by the one or more property computational models may include a third value of the third property exhibited by the first molecule design exhibiting the first value of the first property and the second value of the second property. Moreover, the first utility metric associated with the first molecule design may be indicative of how much the first property, the second property, and the third property of the first molecule design improve over the first property, the second property, and the third property of the one or more baseline molecules.

In some example embodiments, the partial ordering, which prioritizes the first property over the second property, may further include the third property. In some cases, the selection engine may impose the partial ordering in order to prioritize a combination of the first property and the third property over the second property. In this particular scenario, the first property and the third property of the first molecule design may be required to satisfy the first criteria before the first molecule design is evaluated to determine whether the second property of the first molecule design satisfies the second criteria. Alternatively and/or additionally, the selection engine may impose the partial ordering in order to prioritize the first property over the second property, which is further prioritized over the third property. In this case, the first property of the first molecule design may be required to satisfy a first criterion before the first molecule design is evaluated for the second property and the second property of the first molecule design may be further required to satisfy a second criterion before the first molecule design is further evaluated to determine whether the third property of the first molecule design satisfies a third criterion. Referring again to the antibody design example, the selection engine may require that the expression level of the first molecule design to satisfy a first criteria before the first molecule design is evaluated for its binding affinity to a target antigen. Moreover, the binding affinity of the first molecule design may be further required to satisfy a second criterion before the selection engine evaluates its various developability traits such as specificity, thermostability, and/or the like. By including the third property, the selection engine may ensure that the first molecule design is selected as a candidate for synthesis and testing is a joint positive molecule design that meets specific criteria with respect to the first property, the second property, and the third property.

As noted, in some example embodiments, the selection engine may perform multi-objective optimization, such as multi-objective Bayesian optimization, across multiple partially-ordered, mixed-variable properties (or objectives). This framework may be reflective of some scenarios in drug design where a molecule design may be required to satisfy a first property (e.g., expression) before the molecule design is evaluated for a second property (e.g., affinity) and/or a third property (e.g., specificity). As described in more details below, multi-objective optimization (e.g., multi-objective Bayesian optimization) may include imposing, during drug design, a partial ordering that prioritizes the satisfaction of the first property (e.g., expression) over the satisfaction of the second property (e.g., affinity) and/or the third property (e.g., specificity). For example, for each molecule design, the selection engine may modify the posterior probability distribution of each objective (e.g., determined by one or more probabilistic surrogate models) such that the properties exhibited by the molecule design are modeled as zero-inflated distributions (a mixture of zero values and a continuous distribution of non-zero values) and certain properties are prioritized over others. In doing so, the selection engine is able to identify significantly more joint positive molecule designs, as in molecule designs that satisfy criteria across every property being improved, than conventional techniques such as standard Bayesian optimization. Thus, the selection engine increases or maximizes the likelihood that better molecule designs are selected for in vitro and/or in vivo assessment. In particular, the selection of molecule designs from a current design iteration may leverage experimental knowledge from prior design iterations such that candidates with incrementally better properties are selected over successive design iterations.

FIG. 1 depicts a system diagram illustrating an example of a molecule design system 100, in accordance with some example embodiments. Referring to FIG. 1 the molecule design system 110 may include a molecule design engine 110, a selection engine 120, one or more wet lab equipment 130, and a client device 140. As shown in FIG. 1, the molecule design engine 110, the selection engine 120, the one or more laboratory equipment 130, and the client device 140 may be communicatively coupled via a network 150. The one or more laboratory equipment 130 may include any wet lab and dry lab equipment capable of performing in vitro measurements and/or in vivo characterizations. Examples of the one or more laboratory equipment 130 may include sequencers, mass spectrometers, centrifuges, and/or the like. The client device 140 may be a processor-based device including, for example, a workstation, a desktop computer, a laptop computer, a smartphone, a tablet computer, a wearable apparatus, and/or the like. The network 150 may be a wired network and/or a wireless network including, for example, a local area network (LAN), a virtual local area network (VLAN), a wide area network (WAN), a public land mobile network (PLMN), the Internet, and/or the like.

Referring again to FIG. 1, the molecule design engine 110 may apply a molecule design computational model 115 to generate multiple molecule designs including, for example, a first molecule design 160a, a second molecule design 160b, and/or the like. For example, in some cases, the molecule design computational model 115 may be a machine learning model trained to learn a data distribution corresponding to a reduced dimension representation of the composition and/or structure of various known molecules such as protein sequences. In some cases, the data distribution may be a topological space (e.g., a manifold) occupied by the known molecules that describes the relationships that exist therebetween. The molecule design computational model 115 may generate each of the first molecule design 160a and the second molecule design 160b by sampling the data distribution (e.g., the topological space). For instance, in some cases, the first molecule design 160a and the second molecule design 160b may each be a protein sequence corresponding whose reduced dimension representation occupies the data distribution (e.g., the topological space).

In some example embodiments, the molecule design engine 110 may be capable of generating a large quantity of molecule designs but not every molecule design generated by the molecule design engine 110 may undergo in vitro and in vivo assessment. Instead, the selection engine 120 may perform one or more active learning iterations in order to identify, for synthesis and testing by the one or more laboratory equipment 130, one or more joint positive molecule designs that meets specific criteria with respect to multiple properties. In some cases, the one or more criteria associated with a property may include the value of the property satisfying one or more thresholds, falling within one or more intervals of values, or being a member of a set. For example, in the case of antibody design, the selection engine 120 may perform one or more active learning iterations in order to identify one or more molecule designs that exhibit a sufficient expression level as well as adequate binding affinity towards a target antigen. In some cases, the selection engine 120 may further perform the one or more iterations of active learning in order to identify one or more molecule designs that, in addition to having a sufficient expression level and adequate binding affinity, further exhibit certain developability traits such as specificity, thermostability, and/or the like.

FIG. 2A depicts a flowchart illustrating an example of a process 200 for molecule design with multi-objective optimization of partially ordered, mixed-variable properties, in accordance with some example embodiments. Referring to FIGS. 1-2, the process 200 may be performed by the molecule design engine 110 and the selection engine 120 to identify, for example, a subset of the molecule designs generated by the molecule design engine 110 as candidates for in vitro and/or in vivo evaluation.

At 202, the molecule design engine 110 may generate a plurality of molecule designs. In some example embodiments, the molecule design engine 110 may apply the molecule design computational model 115, to generate a plurality of molecule designs including, for example, the first molecule design 160a, the second molecule design 160b, and/or the like.

At 204, the selection engine 120 may determine, for each molecule design of the plurality of molecule designs, a utility metric corresponding to a magnitude to which a combination of properties exhibited by each molecule design improves upon the combination of properties exhibited by one or more baseline molecule designs. In some example embodiments, the selection engine 120 may determine, for each of the plurality of the molecule designs generated by the molecule design engine 110, a corresponding utility metric indicative of how much the combination of properties (e.g., expression, binding affinity, specificity and thermostability, and/or the like) exhibited by each molecule design improves upon the same combination of properties exhibited by one or more baseline molecules. For example, in some cases, the selection engine 120 may determine, for the first molecule design 160a, a first utility metric indicative of a first magnitude to which the combination of properties exhibited by the first molecule design 160 improves upon the combination of properties exhibited by one or more baseline molecules designs. Furthermore, the selection engine 120 may determine, for the second molecule design 160b, a second utility metric indicative of the second magnitude to which the properties of the second molecule design 160b improves upon those of the baseline molecule designs which may include, in some cases, the first molecule design 160a.

At 206, the selection engine 120 may select, based at least on the utility metric associated with each molecule design of the plurality of molecule designs, one or more molecule designs as candidates for synthesis and testing. For example, in some cases, the selection engine 120 may identify the first molecule design 160a and/or the second molecule design 160b as candidates for synthesis and testing if the respective utility metrics satisfy one or more thresholds. Alternatively and/or additionally, the selection engine 120 may select, from the plurality of molecule designs generated by the molecule design engine 110, an N quantity of molecule designs having a highest utility metric as candidates for synthesis and testing. In this case, the first molecule design 160a and/or the second molecule design 160b may be selected as candidates for synthesis and testing if the first molecule design 160a and/or the second molecule design 160b are part of the N quantity of molecule designs having the highest utility metric amongst the plurality of molecule designs generated by the molecule design engine 110. In some cases, in addition to the utility metric associated with each of the first molecule design 160a and the second molecule design 160b, the selection engine 120 may impose additional conditions when selecting the first molecule design 160a and/or the second molecule design 160b as candidates for synthesis and testing. For instance, in the case of antibody design, the selection engine 120 may further require the presence (or absence) of certain amino acid residues (or sequences of amino acid residues) when selecting the first molecule design 160a and/or the second molecule design 160b as candidates for synthesis and testing.

FIG. 2B depicts a flowchart illustrating another example of a process 250 for molecule design with multi-objective optimization of partially ordered, mixed-variable properties, in accordance with some example embodiments. Referring to FIGS. 1 and 2A-2B, the process 250 may be performed, for example, by the selection engine 120 to determine the utility metric of each molecule design generated by the molecule design engine 110. In some cases, the process 250 may implement at least a portion of operation 204 of the process 200 shown in FIG. 2A.

At 252, the selection engine 120 may receive a molecule design. For example, in some cases, the selection engine 120 may receive, from the molecule design engine 110, the first molecule design 160a generated by the molecule design computational model 115.

At 254, the selection engine 120 may apply one or more property computational models to determine a first probability of the molecule design exhibiting a first property and a second probability of the molecule design exhibiting a second property. For example, in some cases, a first property computational model may be applied to determine a first probability of the first molecule design 160a exhibiting a first property by at least enumerating the probability of occurrence of each possible value of the first property of the first molecule design 160a. In some cases, the first property computational model or a second property computational model may be applied to determine a second probability of the first molecule design 160a exhibiting a second property by at least enumerating the probability of occurrence of each possible value of the second property of the first molecule design 160a. In some cases, multiple property computational models (e.g., an ensemble of property computational models) may be applied to determine the value of each property of the first molecule design 160a.

At 256, the selection engine 120 may determine, based at least on an output of the one or more property computational models, a plurality of predictive samples associated with the molecule design in which each predictive sample includes a first value of the first property exhibited by the molecule design and a second value of the second property exhibited by the molecule design having the first value for the first property. For example, in some cases, the output of the one or more property computational models may include multiple intermediate posterior samples, each of which including a first value of the first property exhibited by the first molecule design 160a and a second value of the second property exhibited by the first molecule design 160a. The intermediate posterior samples associated with the first molecule design 160a may correspond to a distribution of the second values of the second property exhibited by the first molecule design 160a across the first values of the first property exhibited by the first molecule design 160a.

Figure 4:
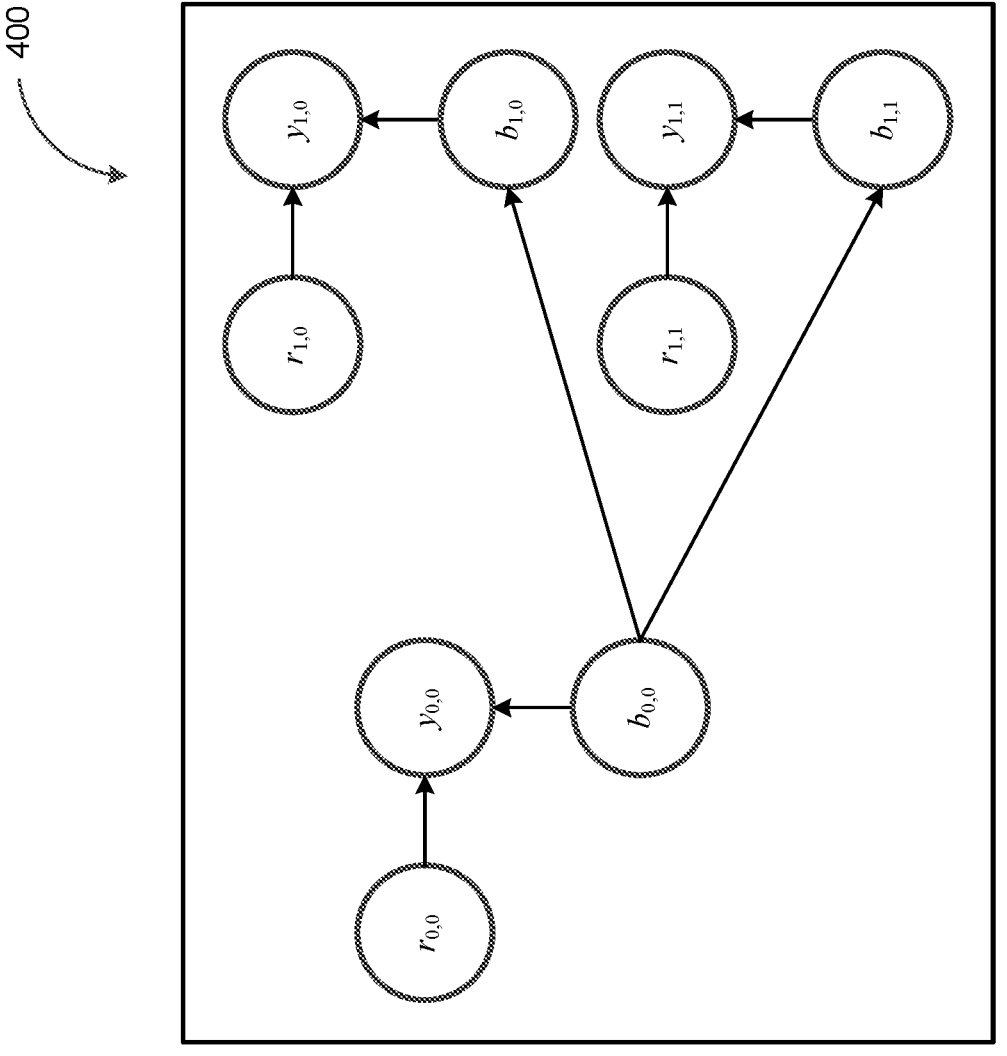
FIG. 4 depicts a schematic diagram illustrating an example of a hierarchy associated with the properties of a molecule design, in accordance with some example embodiments.

At 258, the selection engine 120 may identify, within the plurality of predictive samples, a set of predictive samples in which the first value of the first property satisfies a criterion. In some example embodiments, the selection engine 120 may determine a utility metric indicative of the magnitude to which the first property and the second property of the first molecule design 160a improve upon the first property and the second property of one or more baseline molecule designs. Moreover, the selection engine 120 may impose a partial ordering to prioritize, for example, the first property over the second property, when determining the utility metric associated with the first molecule design 160a. To further illustrate, FIG. 4 depicts a schematic diagram illustrating an example of a hierarchy 400 in which a first property $y_{0,0}$ of the first molecule design 160a is prioritized over a second property $y_{1,0}$ as well as a third property $y_{1,1}$ of the first molecule design 160a. The example of the hierarchy 400 shown in FIG. 4 includes three properties $y_{l,m}$ distributed over two levels indexed by l. Properties occupying the same level of the hierarchy 400 are further indexed by m. The arrows from the first property $y_{0,0}$ to each of the second property $y_{1,0}$ and the third property $y_{1,1}$ may signify a dependency, such as an experimental and/or biological dependency, therebetween. Alternatively and/or additionally, the arrows from the first property $y_{0,0}$ to each of the second property $y_{1,0}$ and the third property $y_{1,1}$ may signify a prioritization of the first property $y_{0,0}$ over each of the second property $y_{1,0}$ and the third property $y_{1,1}$. As explained in more detailed below, the arrows from the output $r_{l,m}$ of the probabilistic regressor model 315 and from the predictive samples $b_{\{l,m\}}$ output by the probabilistic binary classifier 313 to the property $y_{l,m}$ indicate that each $y_{l,m}$ is modeled as zero-inflated, where $b_{l,m}$ governs the zero events and $r_{l,m}$ governs the continuous non-zero events.

At 260, the selection engine 120 may determine, based at least on the set of predictive samples, a utility metric corresponding to an expected improvement in the first property and the second property of the molecule design over the first property and the second property of one or more baseline molecule designs. For example, in some cases, the selection engine 120 may determine a utility metric indicative the magnitude to which the first property and the second property of the first molecule design 160a improve upon the first property and the second property of one or more baseline molecules designs. Moreover, the selection engine 120 may impose a partial ordering that prioritizes the first property over the second property by at least subjecting the intermediate posterior samples associated with the first molecule design 160a to a resampling in order to generate multiple corresponding posterior samples. These posterior samples then undergo a multi-objective acquisition function to determine the utility metric of the first molecule design 160a. Examples of the multi-objective acquisition function applied to determine the utility metric of the first molecule design 160a may include expected hypervolume improvement (EHVI), noisy expected hypervolume improvement (NEHVI), Pareto efficient global optimization (ParEGO), max-value entropy search method (MESMO), joint entropy search (JES), and/or the like.

Figure 3:
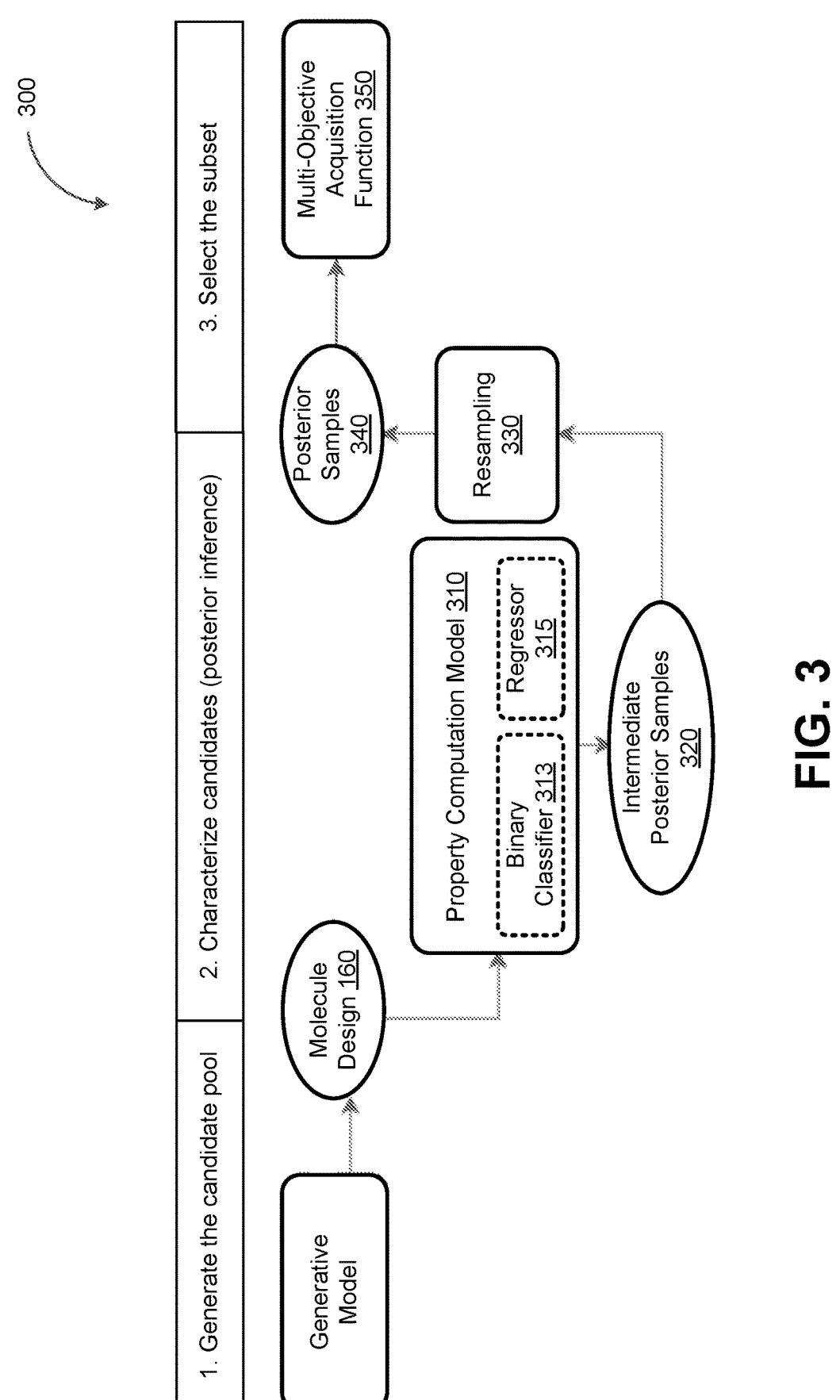
FIG. 3 depicts a block diagram illustrating a molecule design pipeline with multi-objective optimization of partially ordered, mixed-variable properties, in accordance with some example embodiments.

FIG. 3 depicts a schematic diagram illustrating an example of a molecule design pipeline 300, in accordance with some example embodiments. As shown in the molecule design pipeline 300 depicted in FIG. 3, the selection engine 120 may apply one or more property computational models 310 to determine, for example, a first probability of the first molecule design 160a exhibiting a first property and a second probability of the first molecule design 160b exhibiting a second property. In some cases, the one or more property computational models 310 may output a first probability distribution that indicates the first probability of the first molecule design 160a exhibiting the first property by at least enumerating the probability of occurrence of each possible value of the first property exhibited by the first molecule design 160a. Furthermore, in some cases, the one or more property computational models 310 may output a second probability distribution that indicates the second probability of the second molecule design 160a exhibiting the second property by at least enumerating the probability of occurrence of each possible value of the second property exhibited by the first molecule design 160a.

In some example embodiments, the one or more property computational models 310 may be implemented as zero-inflated probabilistic surrogate models including a probabilistic binary classifier 313 and a probabilistic regressor model 315. Moreover, in some cases, the one or more property computational models 310 may include a separate property computational model trained to determine the probability of the first molecule design 160a exhibiting each individual property. For example, the one or more property computational models 310 may include a first property computational model trained to determine the first probability of the first molecule design 160a exhibiting the first property and a second property computational model trained to determine the second probability of the first molecule design 160a exhibiting the second property. In some cases, the one or more property computational models 310 may include at least one property computational model trained to determine the probability of the first molecule design 160a exhibiting multiple properties including, for example, the first property, the second property, and/or the like. Furthermore, in some cases, the one or more property computational models 310 may include multiple property computational models (e.g., an ensemble of property computational models) trained to determine the probability of the first molecule design 160a exhibiting the same property. For instance, the one or more property computational models 310 may include the first property computational model as well as a third property computational model, each of which being trained to determine the first probability of the first molecule design 160 exhibiting the first property.

The inclusion of multiple property computational models (or ensembles of property computational models) for a single property may compensate for at least some of the uncertainty that may be present in the output of individual property computational models. For example, in some cases, the output of an individual property computational model may be less uncertain (or having a higher confidence of being accurate) for some molecule designs encountered by the property computational model and more uncertain (or having a lower confidence of being accurate) for other molecule designs encountered by the property computational model. Alternatively and/or additionally, the output of one individual property computational model may be less uncertain (or having a higher confidence of being accurate) for a particular molecule design) than the output of another individual property computational model for the same molecule design. As such, when multiple property computational models (or an ensemble of property computational models) are applied to determine the property of a molecule design, the lower uncertainty in the output of some property computational models may compensate for the higher uncertainty in the output of other property computational models.

Referring again to FIG. 3, the output of the one or more property computational models 310 may include a plurality of intermediate posterior samples 320. Each sample of the plurality of intermediate posterior samples 320 may include a first value of the first property exhibited by the first molecule design 160a and a second value of the second property exhibited by the first molecule design 160b. The plurality of intermediate posterior samples 320 may correspond to a distribution of the second values of the second property exhibited by the first molecule design 160a across the first values of the first property exhibited by the first molecule design 160a. For example, if the first property is expression level and the second property is binding affinity, each intermediate posterior sample may include a first value of expression level exhibited by the molecule design and a second value of binding affinity that is exhibited by the molecule design having the first value for expression level. The plurality of intermediate posterior samples 320 may thus enumerate the distribution of different expression levels across the different binding affinities exhibited by the molecule design.

In some example embodiments, the selection engine 120 may impose a partial ordering that prioritizes the first property over the second property by at least subjecting the intermediate posterior sample 320 to a resampling 330 to generate a plurality of posterior samples 340. A multi-objective acquisition function 350 may be applied to the posterior samples 340 to determine the utility metric of the first molecule design 160a. Examples of the multi-objective acquisition function 350 may include expected hypervolume improvement (EHVI), noisy expected hypervolume improvement (NEHVI), Pareto efficient global optimization (ParEGO), max-value entropy search method (MESMO), joint entropy search (JES), and/or the like. The resampling 330 may transform any intermediate posterior sample in which the first value of the first property fails to satisfy one or more criteria to preclude these intermediate posterior samples from contributing to the utility metric of the first molecule design 160a.

Figure 5A:
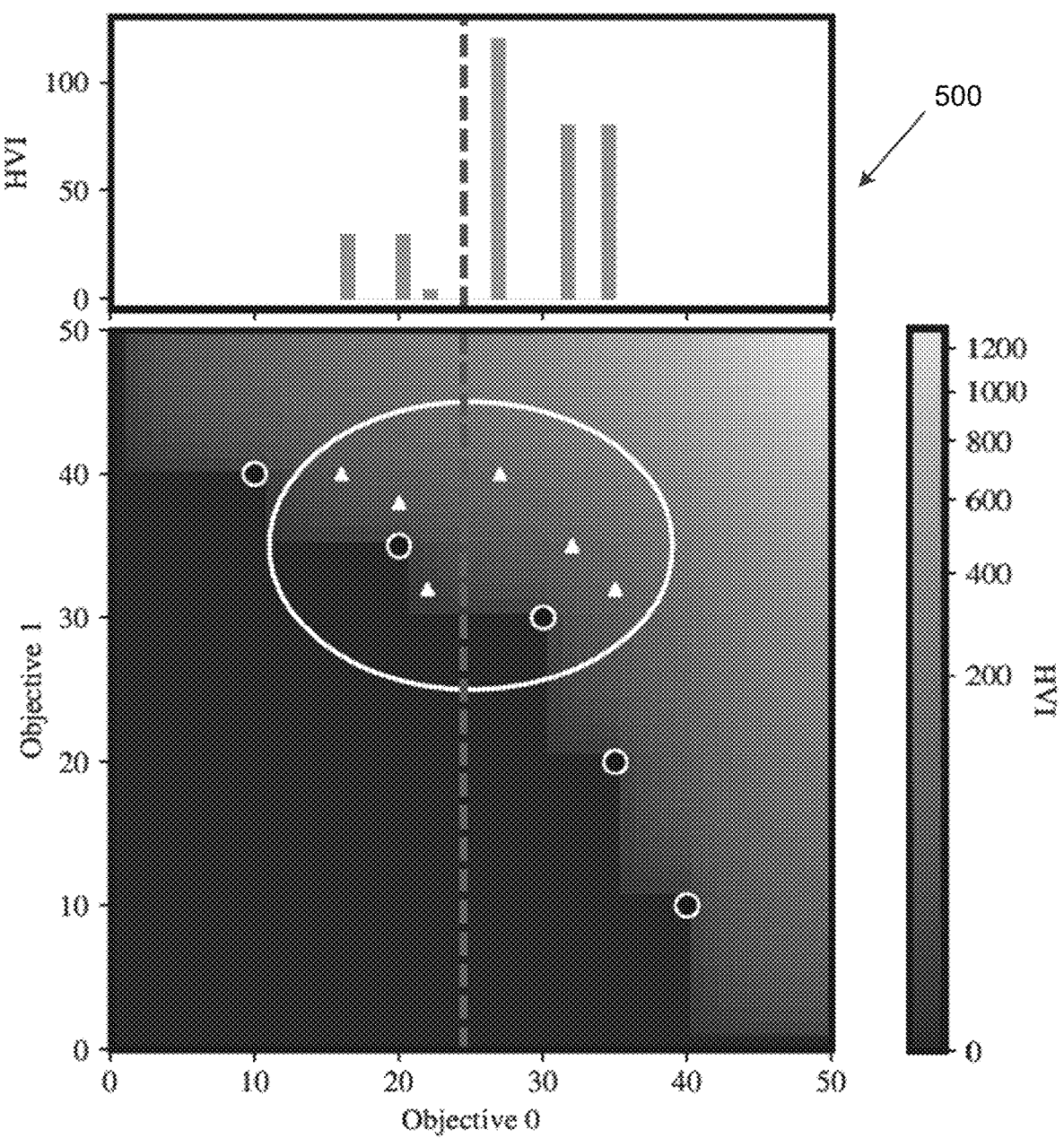
FIG. 5A depicts graphs illustrating the effect of resampling the surrogate posteriors on an example of an acquisition function, in accordance with some example embodiments.
Figure 5B:
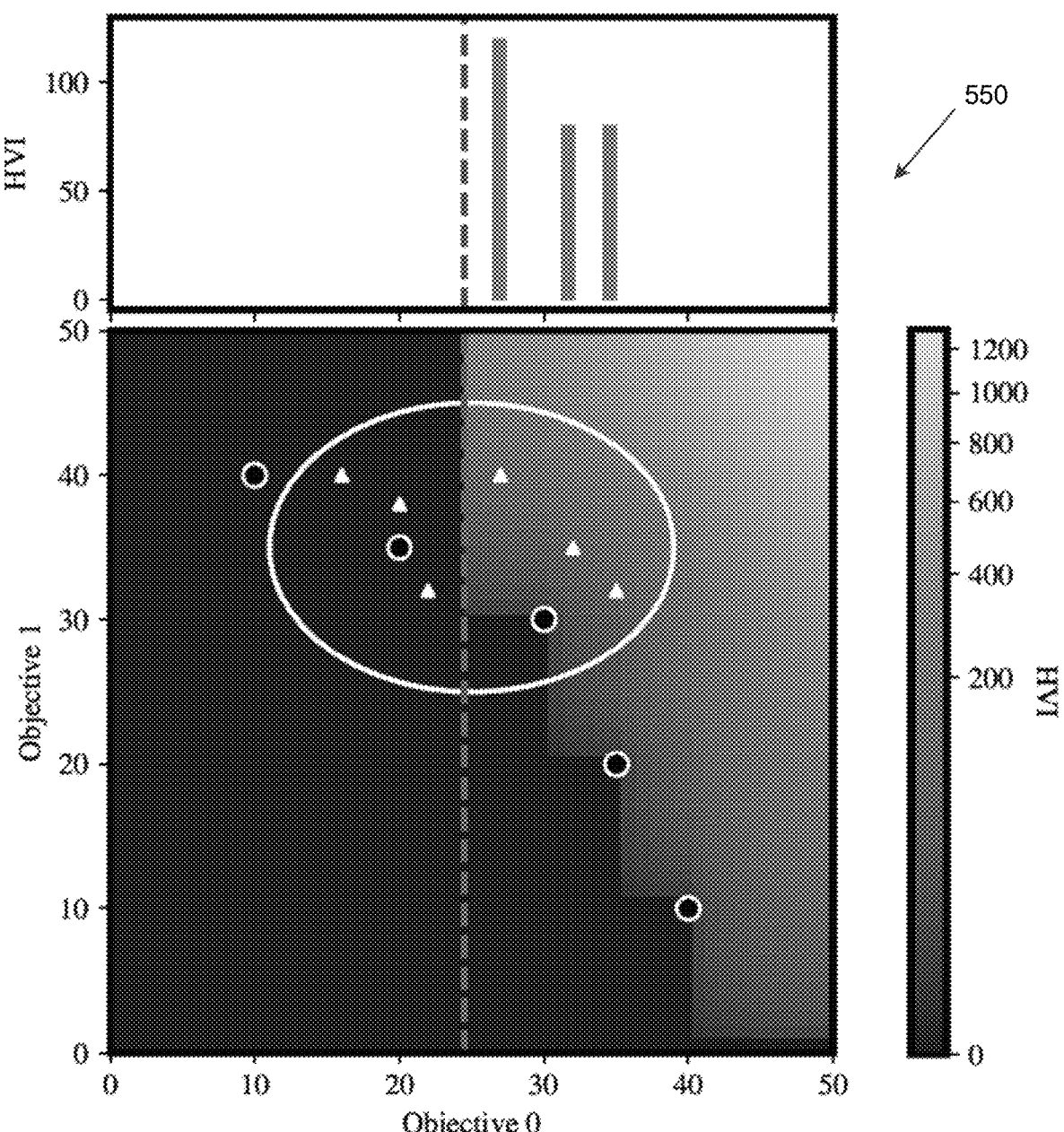
FIG. 5B depicts graphs illustrating the effect of resampling the surrogate posteriors on an example of an acquisition function, in accordance with some example embodiments.

To further illustrate, FIGS. 5A-B depict the effect of the resampling 330 on the intermediate posterior samples 320 output by the one or more property computational models 310. The dashed lines in FIGS. 5A-B represents the criterion (e.g., threshold) for Objective 0 such that the molecule designs selected as candidates for synthesis and testing should increase or maximize Objective 1 while meeting this criterion in Objective 0. The dots in FIGS. 5A-B constitute individual baseline molecule designs forming the baseline Pareto front. The different shading in the grid indicate hypervolume improvement (HVI) computed from each posterior sample at the given location in the objective space.

Consider six intermediate posterior samples 320 (triangles) from the posterior (white contour) shown in their default state in the graph 500 in FIG. 5(a). As shown in graph 550 in FIG. 5(b), the resampling 330 may transform the intermediate posterior samples 320 that fails to meet the criterion (e.g., falls below the threshold) in Objective 0 such that their hypervolume improvement (HVI) contribution is zero. That is, the values of the hypervolume improvement (HVI) for those intermediate posterior samples 320 that fail to meet Objective (0) (e.g., the dotted vertical line), which are not zero in the default state shown in graph 500 in FIG. 5(a), are set to zero as a result of the resampling 330 as shown in graph 550 in FIG. 5(b).

In some example embodiments, the utility metric output by the multi-objective acquisition function 350 for the first molecule design 160a may be indicative of how much the first property and the second property of the first molecule design 160a improve upon the first property and the second property of one or more baseline molecule designs. Furthermore, as a part of the active learning paradigm, the first molecule design 160a may become one of the baseline molecule designs for subsequent selection iterations. For example, the selection engine 120 may determine to select the second molecule design 160b generated by the molecule design engine 110 as another candidate for synthesis based at least on a second utility metric corresponding to an expected improvement in the first property and the second property of the second molecule design 160b over the first property and the second property of the baseline molecule designs which, in this selection iteration, may be updated to include the first molecule design 160a. The values of the first property and the second property associated with the first molecule design 160a may be determined empirically, for example, based on in vitro measurements and/or in vivo characterizations. Alternatively and/or additionally, the values of the first property and the second property of the first molecule design 160a may correspond to the intermediate posterior samples 320 associated with the first molecule design 160a (e.g., an average of the values of the first property and the second property included in the intermediate posterior samples 320).

As noted, the selection engine 120 may determine a utility metric indicative the magnitude to which the first property and the second property of the first molecule design 160a improve upon the first property and the second property of one or more baseline molecules designs. Moreover, as shown in the molecule design pipeline 300 in FIG. 3, the selection engine 120 may impose a partial ordering that prioritizes the first property over the second property by at least subjecting the intermediate posterior sample 320 to the resampling 330 to generate the plurality of posterior samples 340, which then undergo the multi-objective acquisition function 350 to determine the utility metric of the first molecule design 160a. Examples of the multi-objective acquisition function 350 may include expected hypervolume improvement (EHVI), noisy expected hypervolume improvement (NEHVI), Pareto efficient global optimization (ParEGO), max-value entropy search method (MESMO), joint entropy search (JES), and/or the like.

In some example embodiments, the selection engine 120 may compensate for the noise (e.g., measurement errors associated with the laboratory equipment 130) that may be present in observed properties of one or more baseline molecule designs. For instance, in the example shown in FIG. 1 where the selection engine 120 determines a utility metric indicative of the magnitude to which the first property and the second property of the first molecule design 160a improve upon the first property and the second property of one or more baseline molecule designs, the values of the first property and the second property of the one or more baseline molecule designs may be observed in a wet lab and may thus include at least some noise arising from measurement errors associated with the laboratory equipment 130. The effects of this noise may be reduced or minimized by determining the aforementioned utility metric based on the outputs of the one or more property computations models 310 retrained based on the observed values of the first property and the second property of the one or more baseline molecule designs. For example, the retrained property computational models 310 may be applied to determine the values of the first property and the second property for the first molecule design 160a as well as the values of the first property and the second property for the one or more baseline molecule designs. The utility metric for the first molecule design 160a may be determined based on the outputs of the retrained property computational models 310 instead of the observed values of the first property and the second property of the one or more baseline molecule designs.

To further illustrate, FIG. 6A depicts a flowchart illustrating an example of a process 600 for determining the probability of a molecule design exhibiting a property, in accordance with some example embodiments. Referring to FIGS. 1, 2A, and 6A, the process 600 may be performed by the selection engine 120 and may implement, for example, at least a portion of operation 204 of the process 204 shown in FIG. 2A.

At 602, the selection engine 120 may receive, for a baseline molecule design from a previous design iteration, an observed value for a property of the baseline molecule design. In some example embodiments, the molecule designs from a previous design iteration may become baseline molecule designs for a subsequent design iteration. For example, one or more molecule designs from the previous design iterations may be selected for in vitro measurements and/or in vivo characterization of one or more desirable properties (e.g., expression, binding affinity towards another molecule (e.g., a viral antigen, a tumor antigen, and/or the like), lack of non-specificity, stability, lack of immunogenicity, human-ness, lack of self-association, and/or the like). As described in more details below, the observed values of the properties exhibited by these baseline molecule designs may be used during a subsequent design iteration to identify one or more molecule designs whose combination of properties exhibit the most improvement upon the properties of the baseline molecule designs.

At 604, the selection engine 120 may retrain, based at least on the observed value of the property of the baseline molecule design, one or more property computational models trained to determine a probability distribution across different possible values of the property. The observed values of the properties of the baseline molecule designs received in operation 602 may include at least some noise owing to measurement errors present, for example, in the laboratory equipment 130 used to generate the observed values. Accordingly, in some cases, the observed values of the properties of the baseline molecule designs are not used directly to identify molecule designs from the subsequent design iteration whose combination of properties exhibits an improvement or most improvement relative to the properties of the baseline molecule designs. Instead, in some example embodiments, the observed values of the properties of the baseline molecule designs are applied towards retraining the one or more property computational models 310. Doing so may generate a posterior probability distribution for the corresponding properties, for example, by updating the prior probability of these properties based on the observed values.

At 606, the selection engine 120 may apply the one or more retrained property computational models to determine a first value of the property for the baseline molecule design and a second value of the property for a molecule design from a subsequent design iteration. For example, in some cases, the retrained property computational models 310 may be applied to determine the values of the properties for the baseline molecule designs from the previous design iterations as well as the values of the properties for the molecule designs generated during the subsequent design iteration. In the case of expression level, for example, the selection engine 120 may apply the retrained property computational model 310 to determine a first expression level of a baseline molecule design from a previous design iteration as well as a second expression level of a molecule design from a subsequent design iteration. Although the expression level of the baseline molecule design has been observed through wet lab experiments, the utility metric for the molecule design from the subsequent design iteration is not determined directly based on the observed expression level of the baseline molecule design. Instead, as described in more details below, the utility metric of the molecule design from the subsequent design iteration may be determined based on the first expression level of the baseline molecule design determined by the retrained property computational model 310.

At 608, the selection engine 120 may determine, based at least on the first value of the property for the baseline molecule design and the second value of the property for the molecule design from the subsequent design iteration, a utility metric corresponding to a magnitude to which a combination of properties exhibited by the molecule design from the subsequent design iteration improves upon the combination of properties exhibited by the baseline molecule design. In some example embodiments, the selection engine 120 may determine, for the molecule design from the subsequent design iteration, a utility metric corresponding to how much the properties of that molecule design improves upon the properties of the baseline molecule designs from one or more previous design iterations. As noted, even though observed values for the properties of the baseline molecule designs are available, the utility metric for the molecule designs from the subsequent design iteration may be determined based on the outputs of the property computational model 310 retrained based on the observed values instead. Returning to the expression level example, the utility metric for the molecule design from the subsequent design iteration may be determined based on the first expression level of the baseline molecule design and the second expression level of the molecule design from the subsequent design iteration, with both the first expression level and the second expression level being determined by the retrained property computational model 310. In some cases, the utility metric may quantify an expected improvement (EI) for a combination of partially ordered, mixed-value properties exhibited by the molecule design from the subsequent design iteration relative to the baseline molecule design. Moreover, in some cases, the utility metric of the molecule design from the subsequent design iteration may be computed by applying a utility function (e.g., the multi-objective acquisition function 350) including, for example, expected hypervolume improvement (EHVI), noisy expected hypervolume improvement (NEHVI), Pareto efficient global optimization (ParEGO), max-value entropy search method (MESMO), joint entropy search (JES), and/or the like.

In some example embodiments, the selection engine 120 may compensate for the uncertainty that may be the present in the output of each property computational model 310. For example, the selection engine 120 may apply the one or more property computational models 310 to determine a first value of a first property and a second value of a second property exhibited by a molecule design. In some cases, uncertainty in the output of each property computational model 310 may be reduced or minimized by at least applying multiple property computational models 310 (e.g., an ensemble of property computational models) to determine each of the first value of the first property and the second value of the second property for the molecule design. For instance, the selection engine 120 may apply a first property computational model and a second property computational model to assess the first property of the molecule design and the first value of the first property may be determined based on the outputs of the first property computational model and the second property computational model. Similarly, the selection engine 120 may apply a third property computational model and a fourth property computational model to assess the second property of the molecule design and the second value of the second property may be determined based on the outputs of the third property computational model and the fourth property computational model.

To further illustrate, FIG. 6B depicts a flowchart illustrating another example of a process 650 for determining the probability of a molecule design exhibiting a property, in accordance with some example embodiments. Referring to FIGS. 1, 2A, and 6A-B, the process 650 may be performed by the selection engine 120 and may implement, for example, at least a portion of operation 254 of the process 250 shown in FIG. 2B or operation 606 of the process 600 shown in FIG. 6A.

At 652, the selection engine 120 may apply a first property computational model to determine a first value of a property exhibited by a molecule design and a second property computation model to determine a second value of the property exhibited by the molecule design. For example, in the case of expression level, the selection engine 120 may apply an ensemble of property computational models (e.g., a first property computational model, a second property computational model, and/or the like) trained to determine expression level in order to determine the expression level of each molecule design. Alternatively, in the case of binding affinity, the selection engine 120 may also apply an ensemble of property computational models (e.g., a third property computational model, a fourth property computational model, and/or the like) trained to determine binding affinity in order to determine the binding affinity of each molecule design. In some cases, the first value of the property and the second value of the property exhibited by the molecule design may be expressed as a probability distribution. For instance, the output of the first property computational model may include a first probability distribution across the range of possible values for the property (e.g., expression level, binding affinity, and/or the like) while the output of the second property computational model may include a second probability distribution across the range of possible values for the property (e.g., expression level, binding affinity, and/or the like). In some cases, the output of the first property computational model and the second property computational model may be zero-inflated, meaning that the output includes a first value (e.g., a binary value) indicating the presence (or absence) of the property (e.g., expression level, binding affinity, and/or the like) and a second value indicating the magnitude of the property exhibited by the molecule design.

At 654, the selection engine 120 may determine, based at least on the first value and the second value, a third value of the property exhibited by the molecule design for computing a utility metric of the molecule design. The outputs of each probability computation model in the aforementioned ensembles may be associated with at least some uncertainty. In particular, differences in architecture and/or training may give rise to property computational models that are more (or less) certain when applied to different molecule designs. For example, a first property computational model may generate a more certain output for a first molecule design than a second property computational model but the second property computational model may generate a more certain output for a second molecule design than the first property computational model. Accordingly, in some example embodiments, the selection engine 120 may compensate for this uncertainty by at least determining the utility metric of molecule designs based on the outputs of multiple property computational models instead of the output of a single property computational model. In some cases, the value of the property (e.g., expression level, binding affinity, and/or the like) used to determine the utility metric for the molecule design may be determined based on multiple values of the same property as determined by the ensemble of property computational models. For example, in cases where a first property computational model is applied to determine a first value of the property and a second property computational model is applied to determine a second value of the property, the selection engine 120 may determine, based at least on the first value and the second value, a third value for the property for determining the utility metric of the corresponding molecule design. In some cases, the third value of the property may correspond to a mean, a median, a maximum, a minimum, a mode, and/or a range of the first value and the second value.

As described earlier, in some example embodiments, the selection engine 120 may perform multi-objective Bayesian optimization (BO) to trade off exploration (evaluating highly uncertain molecule designs) and exploitation (evaluating molecule designs believed to increase or maximize the objectives) by leveraging the one or more probabilistic surrogate models (e.g., the one or more property computational models 310) and a utility function (e.g., the multi-objective acquisition function 350). If the objective (or property) $f:\chi \to \mathbb{R}$ is a black-box function of the design space $\chi$ that is expensive to evaluate (e.g., in the wet lab), the goal of Bayesian optimization is to efficiently identify a design $x^* \in \mathcal{F}$ that increases or maximizes $f$. Thus, Bayesian optimization (BO) in this context may include leveraging the one or more probabilistic surrogate models (e.g., the one or more property computational models 310) and the utility function (e.g., the multi-objective acquisition function 350) to trade off exploration of the design space $\chi$ to evaluate more uncertain molecule designs (e.g., molecule designs with unknown likelihood of increasing or maximizing $f$) and exploitation of more certain molecule designs that are believed to increase or maximize $f$.

The probabilistic surrogate model (e.g., the property computational model 310) $\hat{f}:\chi \to \mathbb{R}$ may construct the belief about the probability distribution of $f$ based on existing information. For example, where $f$ is the expression level of a molecule design, the probabilistic surrogate model (e.g., the property computational model 310) $\hat{f}:\chi \to \mathbb{R}$ may be trained based on web lab measurements of the expression level exhibited by molecule designs from previous design iterations. Given the presence of observation noise (e.g., measurement errors associated with the laboratory equipment 130), the property computational model 310 may be trained on a noisy dataset available up to a given design iteration t. In other words, each iteration t∈N may be associated with a dataset $D_t=\{(x^{(1)}, y^{(1)}), \ldots, (x^{(N_t)}, y^{(N_t)})\}\in D_t$ where each $y^{(n)}$ is a noisy observation of $f$. Accordingly, the probabilistic surrogate model (e.g., the property computational model 310) $\hat{f}:\chi\to\mathbb{R}$ may be trained to infer the posterior distribution $p(\hat{f}|D_t)$, which quantifies the plausibility of surrogate objectives $\hat{f}\in\mathcal{F}$. In the expression level example, the posterior distribution $p(\hat{f}|D_t)$ quantifies the probability distribution of possible expression levels exhibited by the next batch of molecule designs (e.g., generated by the molecule design computational model 115).

The utility function (e.g., the multi-objective acquisition function 350) $\alpha:\chi\times\mathcal{F}\to\mathbb{R}$ may ingest the posterior distribution $p(\hat{f}|D_t)$ determined by the probabilistic surrogate model (e.g., the property computational model 310) and determine a corresponding utility metric $\alpha$ for each molecule design. In some cases, the utility metric $\alpha$ may quantify the usefulness of each molecule design x. As described in more detail below, the usefulness (or utility) of each molecule design x may correspond to the likelihood of the molecule design exhibiting better properties than molecule designs from previous design iterations. For example, in some cases, molecule designs increasing or maximizing the utility metric $\alpha$ may be selected for further in vitro measurements and/or in vivo characterization. That is, in some cases, the molecule designs that are selected for in vitro measurements and/or in vivo characterization may be identified based on a difference between the expected values for a set of partially-ordered, mixed-variable properties (or objectives) exhibited by each molecule design and the largest values for the same properties (or objectives) observed thus far (e.g., in molecule designs from previous design iterations). The expected values for each property (or objective) may be computed based on the aforementioned posterior distribution inferred by the corresponding property computational model 310.

In some example embodiments, the utility function (e.g., the multi-objective acquisition function 350) may determine an expected improvement (EI) in the properties exhibited by the molecule designs in the current design iteration relative to the properties exhibited by the molecule designs from previous design iterations. Examples of the utility function (e.g., the multi-objective acquisition function 350) a(x) may include expected hypervolume improvement (EHVI), noisy expected hypervolume improvement (NEHVI), Pareto efficient global optimization (ParEGO), max-value entropy search method (MESMO), joint entropy search (JES), and/or the like. In the case of expected improvement (EI), the expected improvement (EI) acquisition function may be obtained by taking $u_{EI}(x, \hat{f}, D_t)=[\hat{f}(x)-max_{(x',y')\in D}y']_+$, where $[\bullet]_+=max(\bullet,0)$. In some cases, the integral may be approximated by Monte Carlo (MC) integration with posterior samples $\hat{f}^{(j)}\sim p(\hat{f}|D_t)$. A maximizer of $\alpha$ may be selected as the molecule design for in vitro measurements and/or in vivo characterization. As described in more details below, actual values of the properties exhibited by this molecule design may be measured (e.g., in a web lab) before the observations are appended to a dataset for retraining the corresponding probabilistic surrogate model (e.g., the corresponding property computational model 310).

As noted, the utility metric $\alpha$ for a molecule design in the current design iteration may be computed relative to the property values of molecule designs from previous design iterations. In some cases, the property values of molecule designs from previous design iterations may be determined based on wet lab measurements. Alternatively, the property values of molecule designs from previous design iterations may be determined by the corresponding probabilistic surrogate models (e.g., the corresponding property computational models 310) after the models have been retrained based on the wet lab measurements of these properties. For example, in some cases, upon querying the probabilistic surrogate model $f$ (e.g., the property computational model 310) for a molecule design and a labeled pair $(x^l, y^l)$ for the design is obtained, for example, from wet lab measurements, those values may be appended to the dataset $D_{t+1}=D_t\cup\{(x', y')\}$ for the next design iteration t+1. The probabilistic surrogate models (e.g., the property computational models 310) may be retrained on this augmented dataset $D_{t+1}$ before being applied to determine the posterior distribution of the corresponding property values for molecule designs from the next design iteration t+1.

When there is a single objective (property) of interest, the best molecule design may be identified based on a ranking of the property values (e.g., highest expression level, highest binding affinity, and/or the like). When there are multiple objectives (or properties) of interest, the best molecule design may not be one having the best values for every objective (or property) at least because a single molecule design that excels in every objective $f$ may not exist. Thus, in a scenario with K objectives (or properties), at least a K quantity of probabilistic surrogate models (e.g., property computational 310) $f_k:\chi\to\mathbb{R}$ may exist for k=1, . . . , K. In some cases, instead of a single molecule design with the best values for every property, the goal of multi-objective optimization (MOO) may be to identify the set of Pareto-optimal tradeoffs such that improving one objective (or property) within the set leads to a worsening another objective (or property). For example, the Pareto-optimal tradeoffs for optimization across expression level and binding affinity may be a set of molecule design in which an improvement in expression level is accompanied by a decrease in binding affinity.

To further illustrate, consider two molecule designs $x^{(1)}$ and $x^{(2)}$ and denote the solution of each design x in the objective space (of K objectives) as $f(x):=[f_1(x), \ldots, f_K(x)]$. In some cases, $f_k(x^{(1)})$ may be said to dominate $f_k(x^{(2)})$, or $f_k(x^{(1)})\succ f_k(x^{(2)})$, if $f_k(x^{(1)})\geq f_k(x^{(2)})$ for all K objectives and $f_k(x^{(1)})\succ f_k(x^{(2)})$ for at least one of the K objectives . . . . The Pareto frontier (PF) may be defined as the set of non-dominated solutions expressed as Equation (1) below.

$$\mathcal{P}^* = \{f(x): x \in X, \nexists x' \in X \text{ s.t. } f(x') \succ f(x)\} \qquad (1)$$

The foregoing formulation of the Pareto-frontier (PF) may give rise to the set of Pareto-optimal designs $\chi^*=\{x:f(x)\in \mathcal{P}^*\}$. The size of $\chi^*$, which is why multi-objective optimization (MOO) determines a finite approximation of the set of Pareto-optimal designs $\chi^*$. within a reasonable number of iterations. One way to measure the quality of an approximate Pareto-frontier (PF) is to compute the hypervolume $HV(P|r_{ref})$ of the polytope dominated by P and bounded from below by a specified reference point, $y_{ref}\in\mathbb{R}^K$, such as the values of the K objectives exhibited by molecule designs from previous design iterations. Denoting this reference point as $HV(\mathcal{P}|y_{ref})$, the expected improvement, such as the expected hypervolume improvement (EHVI), with respect to the existing baseline Pareto front $P_t$ at design iteration t may be denoted as $HVI(\mathcal{P} \mid \mathcal{P}_t, y_{ref}):=HV(\mathcal{P} \cup \mathcal{P} \mid y_{ref})-HV(\mathcal{P} \mid y_{ref})$. As noted, the expected hypervolume improvement (EHVI) acquisition function is one example of the multi-objective acquisition function 350 that may be applied by the selection engine 120. Other examples of the multi-objective acquisition function 350 may include the noisy expected hypervolume improvement (NEHVI) described in more detail below, Pareto efficient global optimization (ParEGO), max-value entropy search method (MESMO), joint entropy search (JES), and/or the like. According to Equation (2) below, the expected hypervolume improvement (EHVI) acquisition function may take the expectation of hypervolume improvement HVI over the posterior distribution $p(f \mid \mathcal{D}_t)$ output by the probabilistic surrogate models (e.g., the property computational models 310). The integral in Equation (2) may be evaluated by drawing samples (e.g., Monte Carlo samples) from the surrogate posterior $\hat{f}_t \sim p(f \mid \mathcal{D}_t)$.

$$\alpha_{EHVI}(x \mid \mathcal{P}_t) = \int HVI(f(x) \mid \mathcal{P}_t) p(f \mid \mathcal{D}_t) df, \quad (2)$$

In the noiseless setting, the observed baseline Pareto front (PF) may be the true baseline Pareto front (e.g., $P_t=\{y:y\in y_t, \exists y'\in y_t \text{ s.t. } y'>y\}$ wherein $y_t:=\{y^{(n)}\}_{n=1}^{N_t}$. This does not, however, hold in many practical applications, where wet lab measurements carry noise, for example, in the form of measurement errors associated with the laboratory equipment 130. For example, given a zero-mean Gaussian measurement process with noise covariance $\Sigma$, the feedback for a molecule design x is $y \sim N(f(x), \Sigma)$, not $f(x)$ itself. To account for this noise, the baseline Pareto front (PF) associated with molecule designs from previous design iterations may correspond to property values determined by the updated probabilistic surrogate models (e.g., the property computational models 310), which have been retrained on the wet lab measurements for those molecule designs. That is, the noisy expected hypervolume improvement (NEHVI) may marginalize over the surrogate posterior at the previously observed points $X_t=\{x^{(n)}\}_{n=1}^{N_t}$ in accordance with Equation (3) below. It should be appreciated that while noisy expected improvement (EI) extends expected improvement to a setting with observational noise (e.g., measurement errors associated with the laboratory equipment 130), the noisy expected hypervolume improvement (NEHVI) extends noisy expected improvement to the optimization of multiple objectives (or properties).

$$\alpha_{NEHVI}(x \mid \mathcal{P}_t) = \int \alpha_{EHVI}(x \mid \mathcal{P}_t) p(f \mid \mathcal{D}_t) df \quad (3)$$

Sequential optimization, or querying $f$ for a single molecule design per iteration, may be impractical for many applications due to the latency in feedback. In protein engineering, for example, it may be necessary to select a batch of molecule designs in a given iteration and wait several months to receive measurements. Jointly selecting a batch of q molecule designs from a large pool of $q'>>q$ candidates may require combinatorial evaluations of the utility function (e.g., the multi-objective acquisition function 350). In the context of optimizing molecule designs based on the gradient of the utility function (e.g., the multi-objective acquisition function 350), sequential greedy selection of q molecule designs in a given design iteration may achieve comparable performance to joint selection of q candidates for a variety of utility functions (e.g., multi-objective acquisition functions 350).

Many molecule design applications require the enforcement of some hierarchy amongst multiple objective properties of interest. In some cases, the partial ordering may arise from an experimental dependency in which a molecule design must satisfy one or more criteria (e.g., pass a certain threshold) in one property before its other properties can be measured. In the context of antibody design, a design candidate is a sequence of amino acids representing an antibody that must first be expressed in cell culture. If the level of expression does not exceed some threshold in mass per volume, the lab cannot produce it in viable amounts and it cannot be assayed for other properties, such as binding affinity to a target antigen. A partial ordering that captures this experimental dependency may take the form: expression→affinity. Experimental dependencies like this creates an asymmetry among the objectives; it reduces the information content of molecule designs that do not express much more than that of designs that do not bind, because non-expressing designs cannot provide binding measurements.

Alternatively, the partial ordering may encode a preference for the types of molecule designs. One or more properties may be prioritized, for example, such that molecule designs that perform poorly in these properties may be rejected no matter how well the molecule designs perform in other properties. In the context of antibody body design, if a molecule design does not bind to the target antigen, it has failed in its primary function and there would be little interest to explore its developability properties, such as specificity to the target antigen and thermostability, even though, unlike for non-expressers, these developability properties often remain measurable. A partial ordering to capture this preference may take the form: expression→affinity→{specificity, thermostability}.

Referring again to the example of the hierarchy 400 shown in FIG. 4, a partial ordering of properties in which some properties are prioritized over others may be expressed as ordered sets of properties: $\{y_{0,0}, \ldots, y_{0,M_0}\} \rightarrow \{y_{1,0}, \ldots, y_{1,M_1}\} \rightarrow \{y_{L,0}, \ldots, y_{L,M_L}\}$, wherein $y_{l,m}$ denotes the property at level $l\in\{0, \ldots, -1\}$ of the hierarchy 400 and $m\in\{0, \ldots, M_{L}-1\}$ is its index among the $M_l$ sibling properties at the same level $l$. Various examples of multi-objective optimization (MOO) described herein, including the foregoing Bayesian optimization, may include prioritizing the properties at level l over those at a subsequent level l+1 such that molecule designs whose level l+1 satisfy their corresponding criteria are rejected if the level l properties of the molecule designs fail to satisfy the corresponding criteria.

Biological properties tend to carry excess zeros, or null values. That is, zero may be the most prevalent values for biological properties such as expression, binding affinity, lack of non-specificity, stability, lack of immunogenicity, human-ness, lack of self-association, and/or the like. For example, in the case of antibody design, a large proportion of molecule designs may not express at all, which contributes to the high incidence of zero values (or null values) for that particular property. The zero-inflated nature of biological properties motivates the use of statistical models that account for large incidences of zeros. For instance, in some example embodiments, the one or more property computation models 310 may be implemented as zero-inflated probabilistic surrogate models. Accordingly, for each objective (or property) $y_k$, the probabilistic binary classifier 313 of the property computation model 310 may assign a binary random variable $b_k \in \{0, 1\}$ to indicate the presence (or absence) of the property $y_k$, thus generating the zero values of the objective $y_k$, while the probabilistic regressor model 115 may generate $r_k \in \mathbb{R}$ corresponding to the remaining dispersion of continuous non-zero values for the same property $y_k$. In some cases, the probabilistic binary classifier 313 may assign the binary random variable $b_k \in \{0, 1\}$ based on whether the property $y_k$ satisfies one or more thresholds. Thus, instead of merely indicating whether the property $y_k$ is present (or absent) outright, it should be appreciated that the output of the probabilistic binary classifier 313 may indicate whether the property $y_k$ is present to a sufficient quantity or level.

In one example where the property computation model 310 is trained to predict the expression level of molecule designs, the output of the property computation model 310 may include a first value determined by the probabilistic binary classifier 313 to indicate whether the expression level of the molecule design satisfies one or more thresholds. Furthermore, the output of the property computation model 310 may include a second value determined by the probabilistic regressor model 115 indicating the expression level of the molecule design in instances where the expression level of the molecule design is determined to satisfied the one or more thresholds (e.g., assigned a value of 1 by the probabilistic binary classifier 313).

To further illustrate, assume $f$ is non-negative (equivalently, that it is bounded from below). Given a dataset $D_t$ available at time t, the probabilistic binary classifier 313 may model the marginal predictive posterior $p(b_k|x)$ of the objective (or property) $y_k$ being a non-zero value.

$$p(b_k \mid x) = \int p(b_k \mid \Phi(f_k(x))) p(f_k \mid \mathcal{D}) df_k \qquad (4)$$

wherein $\Phi: \mathbb{R} \rightarrow (0,1)$ corresponds to the cumulative distribution function (CDF) of the standard normal distribution. The first term in the integral shown in Equation (4) may be a Bernoulli distribution governing the aleatoric uncertainty while the second term may govern the epistemic uncertainty.

Meanwhile, the probabilistic regressor model 315 may model the marginal predictive posterior of the non-zero mode (or the non-zero values) of the property $y_k$, as shown in Equation (5).

$$p(r_k \mid x) = \int p(r_k \mid f_k(x)) p(f_k \mid \mathcal{D}) df_k \qquad (5)$$

The probabilistic regressor model 315 may be trained separately on the non-zero examples of the dataset $\mathcal{D}$. Since Gaussian processes (GPs) may be used as surrogates for Bayesian optimization (BO) and common Gaussian process assumptions fail for sparse, multi-modal data, separating out the non-zero mode of the data can improve posterior inference.

In view of the foregoing, the marginal predictive posterior on each objective (or property) $y_k$ may be a weighted mixture of a delta function and Equation (5) above, where the relative weight on the latter is provided by the Bernoulli parameter in Equation (4). This relationship, which assumes that $p(r_k=0|x)=0$, is shown as Equation (6) below. It should be appreciated although zero-inflated modeling is described for a single objective $y_k$, zero-inflated modeling may be extended to a joint posterior on multiple objectives (or properties) $y \in \mathbb{R}^K$, for example, using a multi-task Gaussian Process (GP).

$$Pr(y_k = y' \mid x) = \begin{cases} p(b_k = y' \mid x) & \text{if } y' = 0 \\ p(r_k = y' \mid x) p(b_k = 1 \mid x) & \text{otherwise} \end{cases} \qquad (6)$$

The aforementioned framework, presented in terms of a zero-inflated, continuous-valued objective (a mixture of a delta function at zero and a continuous distribution), applies to binary-valued objectives and continuous-valued objectives without zero inflation, which can be viewed as specific cases taking $p(r_k|x, D_r, \theta_r)=p(r_k)=N(0, \sigma_2)$ with very small $\sigma$ and $p(b_k=1|x, D_r, \theta_b)=1$, respectively.

In some example embodiments, through the resampling 330 shown in FIG. 3, the selection engine 120 may modify the plurality of intermediate posterior samples 320 output from the one or more property computation models 310 (e.g., zero-inflated probabilistic surrogate models) to further enforce the hierarchical (e.g., parent-child) relationships between various properties. Consider a property $y_k$ and its predecessors, or parent nodes, par(k). Consider one intermediate posterior sample from the plurality of intermediate posterior samples 320 output by the one or more property computation models for a single molecule design with $\beta_k \sim p(b_k|x) \in \{0, 1\}$ and $p_k \sim p(r_k|x) \in \mathbb{R}$ for each $k' \in \{1, \ldots, K\}$. Without any modification, Equation (7) would yield the following sample $\gamma_k$ of $y_k$:

$$\gamma_k = \begin{cases} 0 & \text{if } b_k = 0 \\ \rho_k & \text{if } b_k = 1 \end{cases} \qquad (7)$$

However, the sample $\gamma_k$ is agnostic to any hierarchy, such as the hierarchy 400 shown in FIG. 4, in which some properties are prioritized over others. In some cases, the dependencies present in the hierarchy 400 may be imposed by combining (e.g., multiplying and/or the like) the output of the probabilistic binary classifiers from the parent nodes par(k) with the outputs of the probabilistic binary classifier and the corresponding probabilistic regressor model for the property $y_k$. Accordingly, where the output of the probabilistic binary classifier from one or more parents nodes par(k) "0," indicating that the corresponding molecule design fails to exhibit certain properties occupying the parent nodes par(k), the intermediate posterior sample $\gamma_k$ is then excluded from contributing to the utility metric (e.g., the expected hypervolume improvement (EHVI)) of the corresponding molecule design.

To further illustrate, the selection engine 120 may instead start at the top level of the hierarchy 400, for example, and proceed down the levels therein to impose dependencies between the property $b_k$ and its predecessor or parent properties $\{b_{k'}\}_{k' \in par(k)}$. If $y_k$ is a top-level property, then par(k)=∅ and $\hat{\beta}_k = \beta_k$. Otherwise, $y_k$ has parent properties and $\hat{\beta}_k$ is defined as follows:

$$\hat{\beta}_k = \begin{cases} \beta_k & \text{if } \prod_{k' \in par(k)} \hat{\beta}_k(x) = 1 \\ 0 & \text{otherwise} \end{cases} \qquad (8)$$

The modified binary samples $\{\hat{\beta}_k\}_{k=1}^K$ may then be used to obtain the effective sample $\hat{\gamma}_k$ of $y_k$:

$$\hat{\gamma}_k = \begin{cases} \rho_k & \text{if } \prod_{k' \in par(k)} \hat{\beta}_{k'}(x) = 1 \text{ and } \beta_k = 1 \\ 0 & \text{otherwise} \end{cases} \quad (9)$$

Let $\gamma := [\gamma_1, \ldots \gamma_K] \in R^K$ and $\hat{\gamma} := [\hat{\gamma}_1, \ldots, \hat{\gamma}_K] \in R^K$ and denote the transformation at the sample level described in Equations (8) and (9) as $h : R^K \to R^K$ such that $h(\gamma) = \hat{\gamma}$.

The selection engine 120 may repeat the resampling 330 on the other intermediate posterior samples 320 associated with the molecule design. Denoting each intermediate posterior sample as $\gamma := [\gamma_1, \ldots, \gamma_K] \in \mathbb{R}^K$, each corresponding modified sample vector $\hat{\gamma} := [\hat{\gamma}_1, \ldots \hat{\gamma}_K] \in \mathbb{R}^K$ may then be used to evaluate the multi-objective acquisition function 350 (e.g., the expected hypervolume improvement (EHVI), the noisy expected hypervolume improvement (NEHVI) (Equation (4)), Pareto efficient glo)al optimization (ParEGO), max-value entropy search method (MESMO), joint entropy search (JES), and/or the like) via, for example, Monte Carlo (MC) integration. More precisely, suppose S intermediate posterior samples were drawn in parallel for a design candidate x* (reflecting aleatoric as well as epistemic uncertainties) and the previously observed designs $x_r = \{x^{(n)}\}_{n=1}^N$ (reflecting the aleatoric uncertainty) and denote each draw as $\gamma^*_s$ and $G_s := \{\gamma_s^{(n)}\}_{n=1}^{N_t}$, respectively, for s= ..., S. Then the Monte Carlo approximation of the multi-objective acquisition function (e.g., noisy expected hypervolume improvement (NEHVI) in some cases) may be efficiently evaluated as:

$$\hat{\gamma}^*_s = h(\gamma^*_s), \hat{\gamma}^{(n)}_s = h(\gamma^{(n)}_s) \; \forall_x = 1, \ldots, S, \forall_n = 1, \ldots, N_t \quad (10)$$

$$\propto_{NEHVI} (x^*) \approx \frac{1}{S} \sum_{s=1}^{S} HVI(P_t^{*[s]}, P_t^{[s]} r_{ref}),$$

$$\text{wherein } P_t^{[s]} = \{\gamma_s : \gamma_s \in G_s, \nexists \gamma'_s \in G_s \text{ s.t. } \gamma'_s \succ \gamma_s\} \text{ and}$$

$$P_t^{*[s]} = P_t^{[s]} \cup \{\hat{Y}^*_s\}.$$

Example Tasks for Multi-Objective Optimization (MOO)

The performance of the selection engine 120 was evaluated through simulated active experiments on two synthetic tasks and one real-world antibody design task. For these example use cases, noisy expected hypervolume improvement (NEHVI) (Equation (4)) was used as the multi-objective acquisition function 350. Moreover, the multi-objective acquisition function 350 was evaluated via Monte Carlo integration (Equation (10)). Each experiment tested three types of acquisitions: (1) batched, multi-objective Bayesian optimization (BO) with a partial ordering of properties ("qNEHVI-DAG"), (2) batched, multi-objective Bayesian optimization without any ordering of properties ("qNEHVI"), and (3) random. The primary performance metric is the number of acquired "joint positive" molecule designs which, as noted, refer to molecule designs that meet certain criteria (e.g., exceed chosen thresholds) in every objectives according to the specified partial ordering of the properties. Here, the size of each batch is denoted as q.

Example Task I: Penicillin Production

The first penicillin production task is based on a penicillin production simulator. The two objectives in this example may be defined as reducing or minimizing the carbon dioxide ($CO_2$) byproduct emission while ensuring that the fermentation time is below a set threshold and the yield exceeds a set threshold ($K=3$, $X=R^7$). The latter two objectives may be negated to define a maximization problem and assume the property hierarchy $\{y_{0,0}\} \to \{y_{1,0}\} \to \{y_{2,0}\}$, where $y_{0,0}$=Yield ("Objective 0"), $y_{1,0}$=Negative fermentation time ("Objective 1"), and $y_{2,0}$=Negative $CO_2$ byproduct ("Objective 2"). Zero-mean Gaussian noise was added to the input.

An exact Gaussian Process (GP) may be fit to model $r_k$ and an approximate Gaussian Process may be fit with the variational evidence lower bound (ELBO) to model $b_k$, separately for each Objective k. In this example task, 512 posterior samples was drawn to evaluate qNEHVI.

Figure 7A:
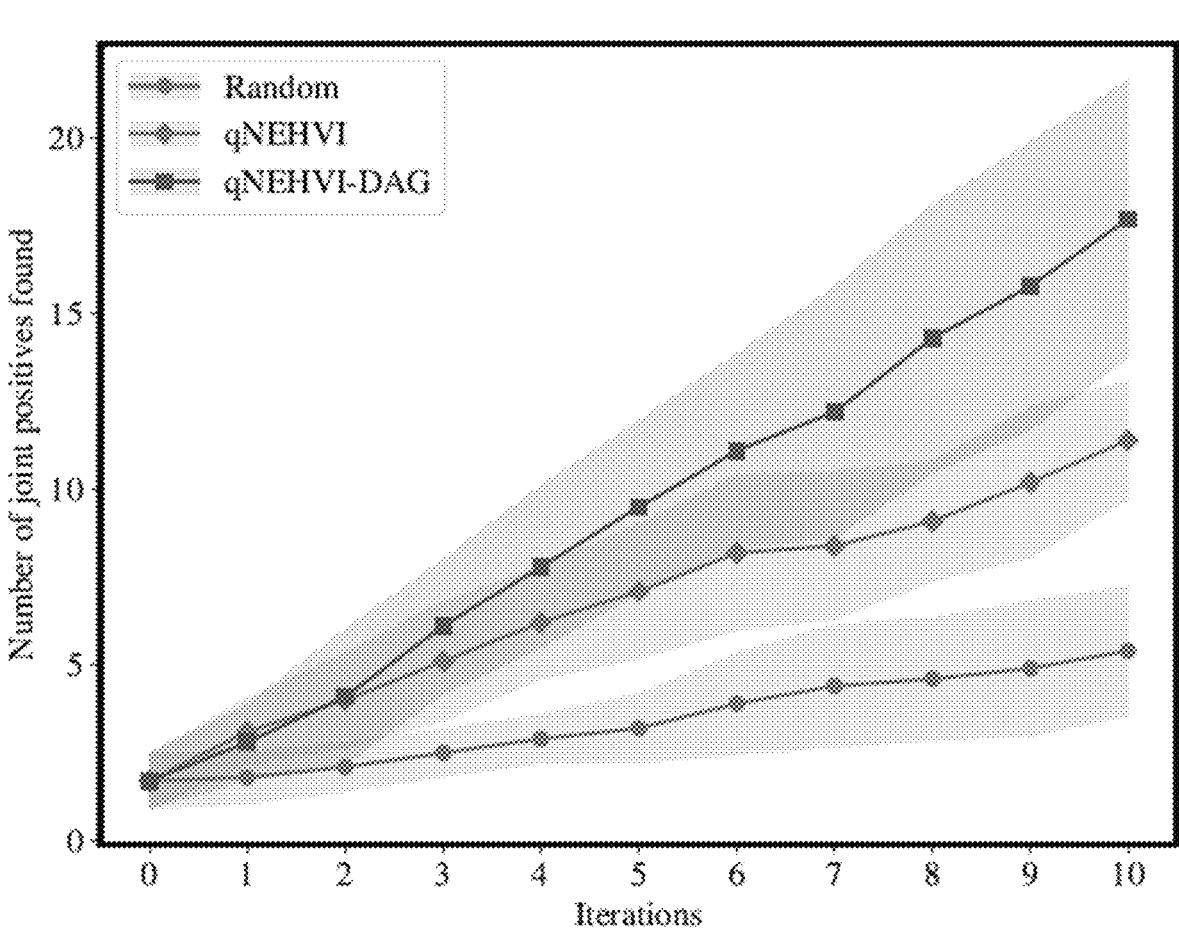
FIG. 7A depicts graphs illustrating the changes in the quantity of joint positive molecule designs over multiple active learning iterations, in accordance with some example embodiments.
Figure 7B:
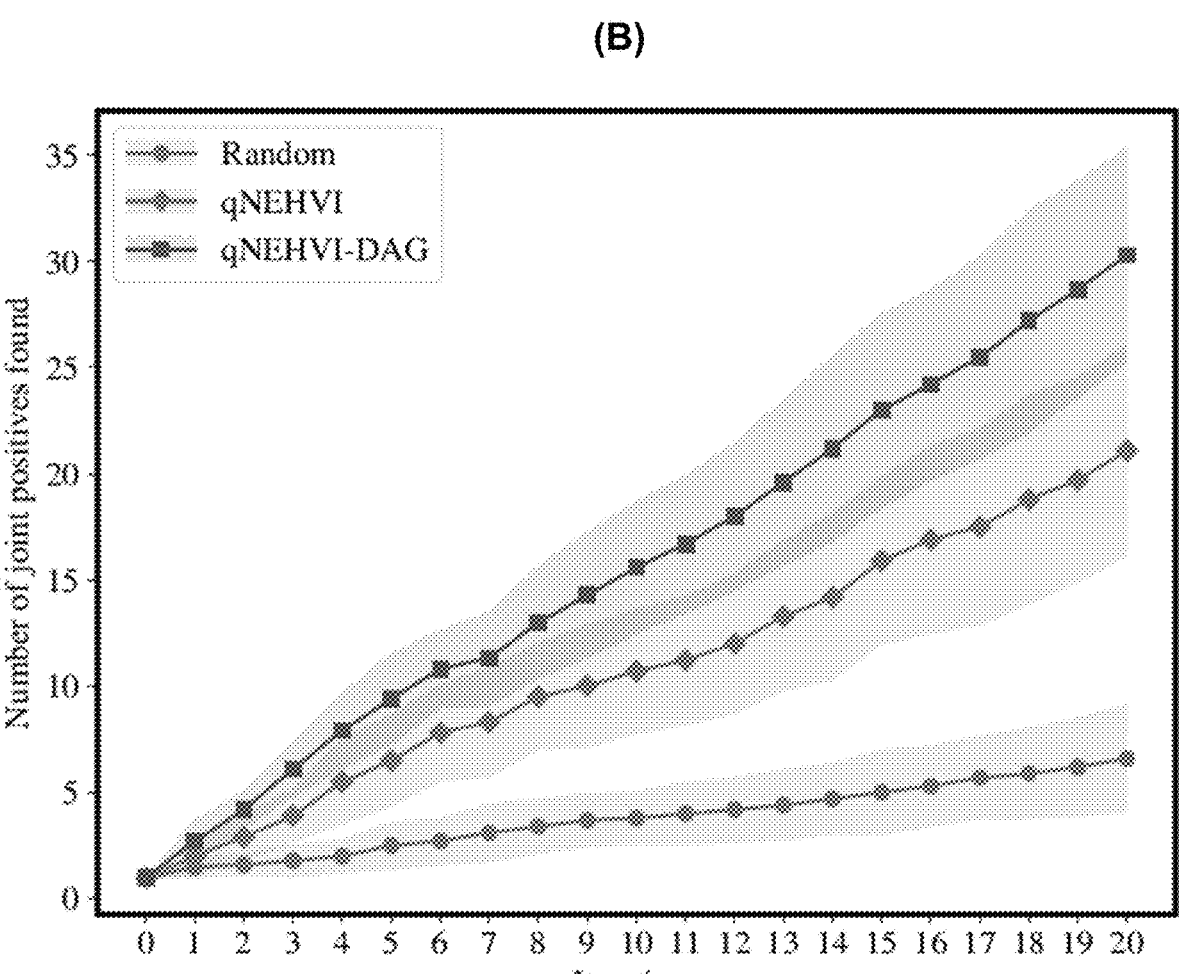
FIG. 7B depicts graphs illustrating the changes in the quantity of joint positive molecule designs over multiple active learning iterations, in accordance with some example embodiments.
Figure 8:
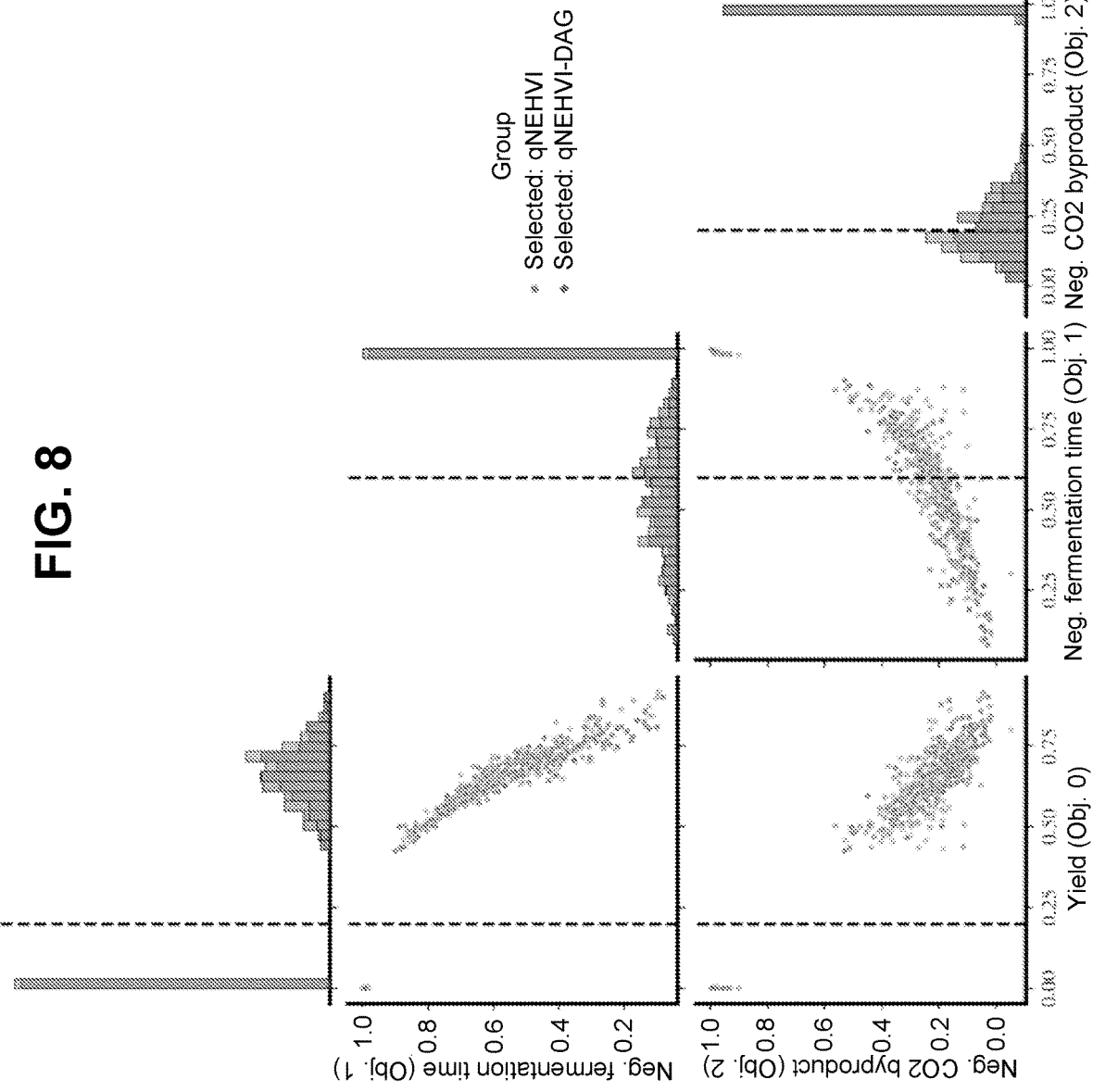
FIG. 8 depicts graphs illustrating the pairwise Pareto front visualization of an example of a penicillin production task, in accordance with some example embodiments.

Ten rounds of simulated active learning may be executed by initializing the one or more property computation models 310 with 8 training points and selecting q=4 out of 80 randomly-sampled pool of candidate points in each iteration. The three acquisition modes (qNEHVI-DAG, qNEHVI, and Random) were subject to the same initial training points and candidate pool each round. The entire experiment was repeated five times. Panel (A) in FIGS. 7A-B shows that qNEHVI-DAG identifies significantly more joint positives than do qNEHVI and Random overactive learning iterations. FIG. 8 compares the qNEHVI and qNEHVI-DAG selections for every pair of objectives, for the final (after Iteration 10) selections stacked across the 5 repeated trials. For every objective, qNEHVI-DAG identifies more examples to the right of the threshold (black dashed lines) than do qNEHVI and Random.

Example Task II: Branin-Currin

The next task is based on an analytic Branin-Currin test function from with $X=R^2$ and $K=2$. The Branin-Currin task is configured to simulate the antibody design task in a controlled environment. Here, the hierarchy of properties may be defined as $\{y_{0,0}\} \to \{y_{1,0}\}$ in which $y_{0,0}$=Dimension 0 ("Objective 0") and $y_{1,0}$=Dimension 1 ("Objective 1"). Objective 0 was transformed into binary values using a set threshold whereas objective 1 was zero-inflated and real-valued. Posterior inference was performed following a similar procedure as the penicillin production task.

Figure 9:
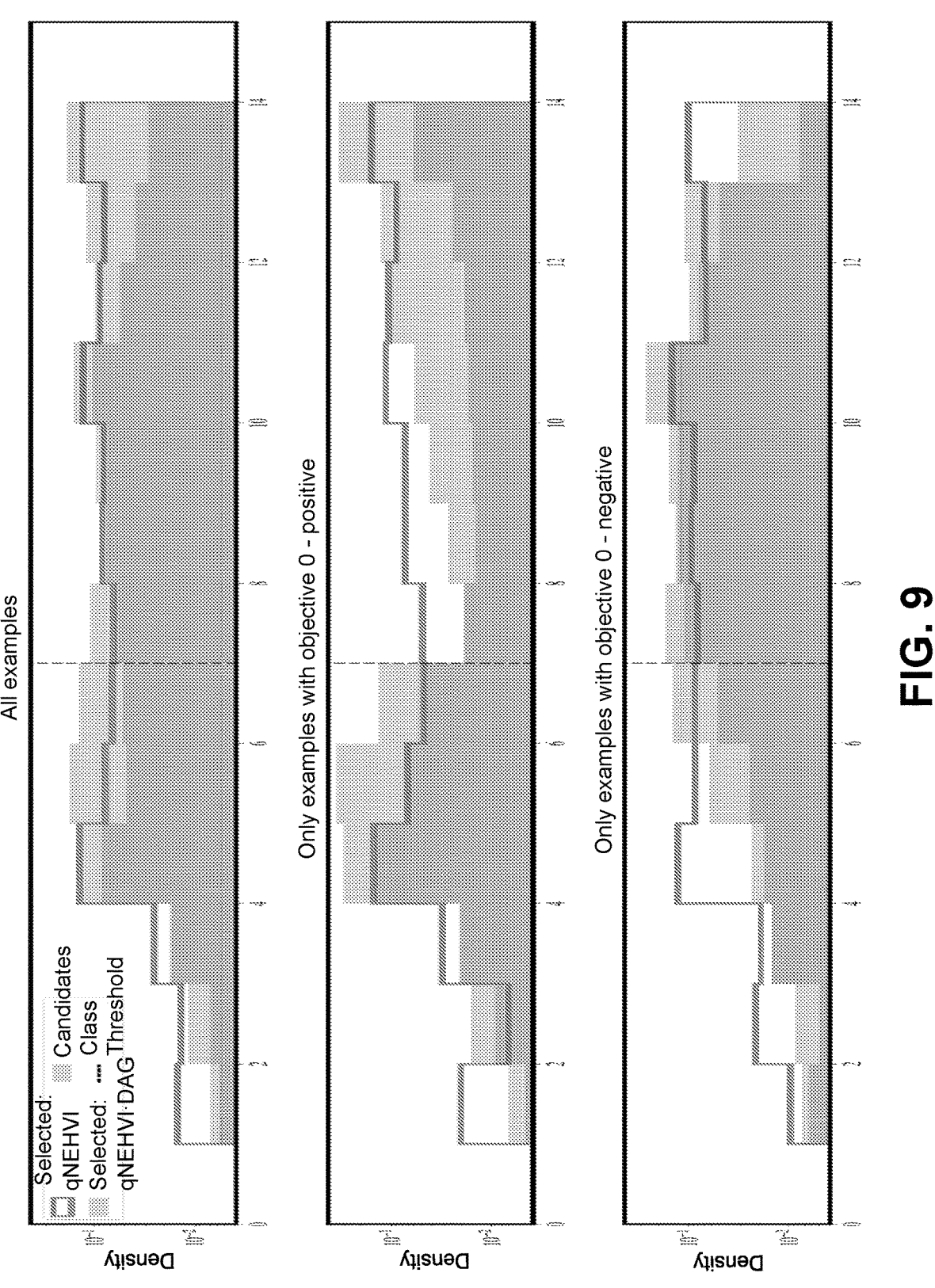
FIG. 9 depicts graphs illustrating the distribution of examples of molecule designs selected as candidates for synthesis and testing, in accordance with some example embodiments.

Here, the selection engine 120 performed 20 rounds of simulated active learning by initializing the one or more property computation models 310 with 6 training points and selecting q=4 out of 40 randomly-sampled pool of candidate points in iteration. The entire experiment was repeated 10 times. Panel (B) in FIGS. 7A-b shows that qNEHVI-DAG identifies significantly more joint positives than do qNEHVI and Random overactive learning iterations. FIG. 9 depicts a comparison between qNEHVI-DAG, qNEHVI, and Random selections for Objective 1, for the final selections stacked across the 10 repeated trials. Overall, qNEHVI-DAG identifies more examples to the right of the threshold (black dashed lines) than do qNEHVI and Random, and the improvement is more pronounced for the identification of joint positives (middle panel).

Example Task III: Antibody Design

The antibody design task is derived from real-world dataset of antibody sequences and their measured in vitro properties for affinity and expression. As in the toy problem, the hierarchy of properties was defined as $\{y_{0,0}\} \to \{y_{1,0}\}$, with $y_{0,0}$=Expression ("Objective 0") and $y_{1,0}$=Affinity ("Objective 1"). Objective 0 was binary-valued (e.g., expressing or not) whereas Objective 1 was zero-inflated and real-valued.

Figure 10A:
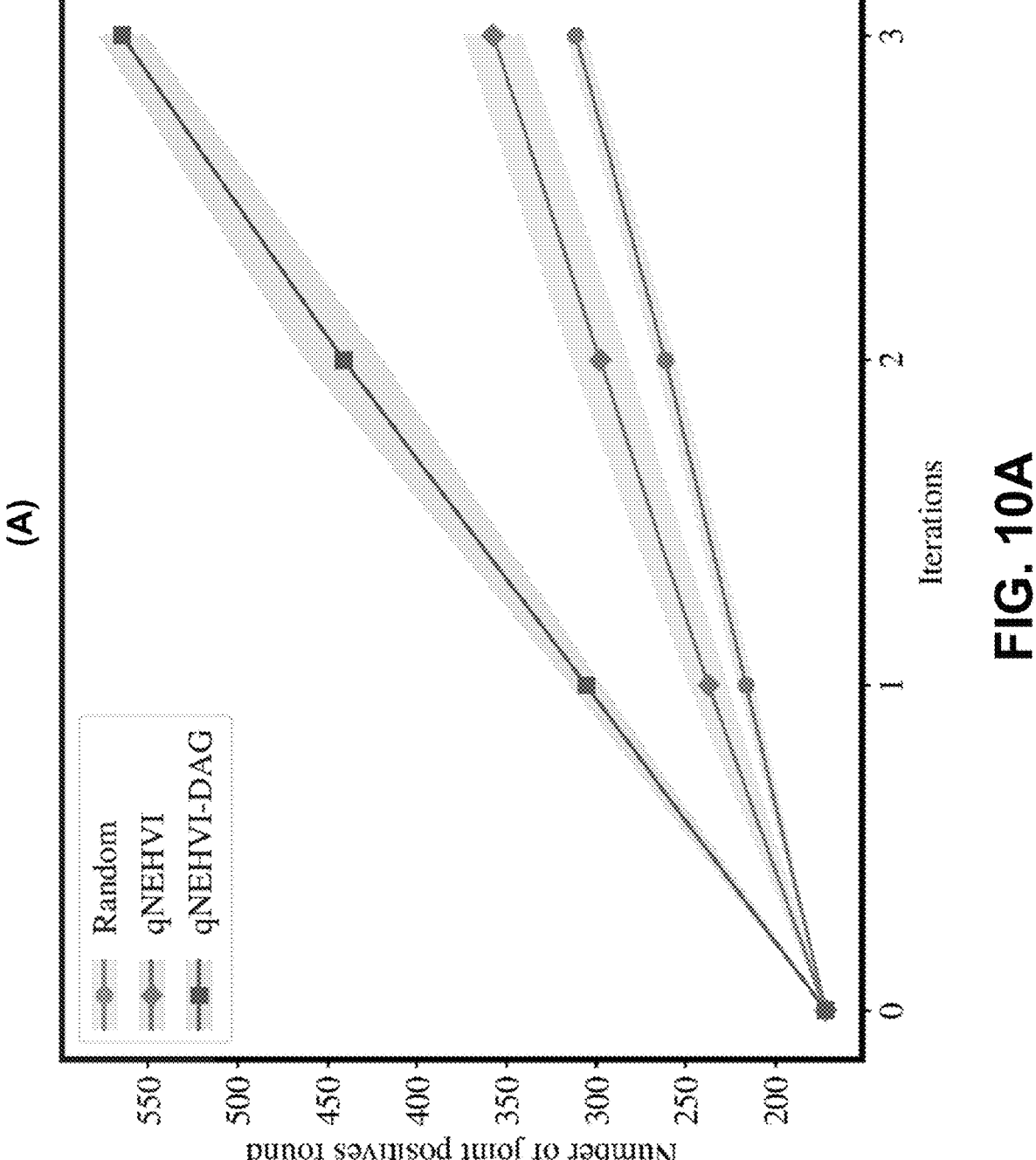
FIG. 10A depicts graphs illustrating the quantity of joint positive molecule designs for an example of an antibody design task and the log posterior density on binding affinity, in accordance with some example embodiments.
Figure 10B:
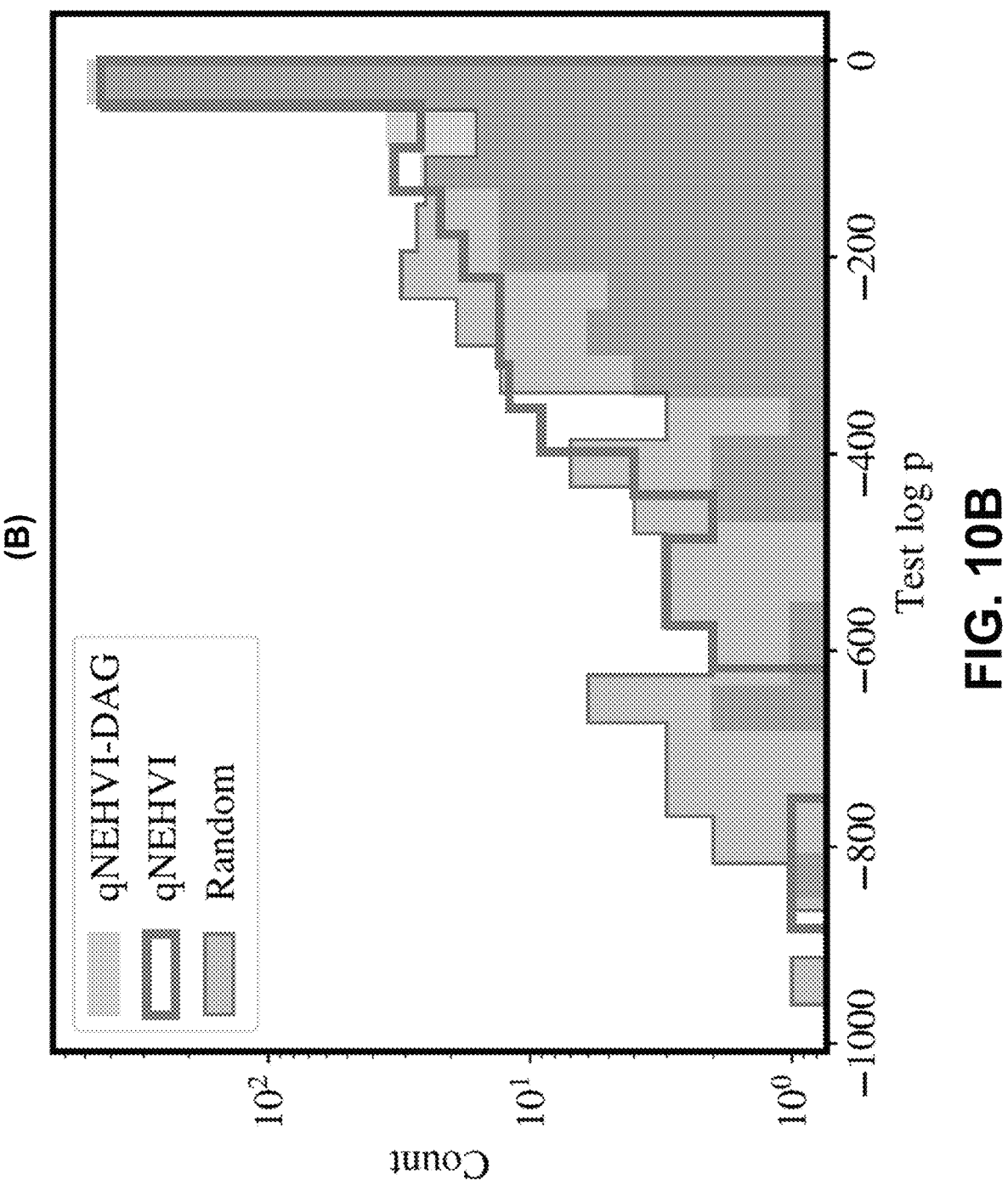
FIG. 10B depicts graphs illustrating the quantity of joint positive molecule designs for an example of an antibody design task and the log posterior density on binding affinity, in accordance with some example embodiments.

The selection engine 120 executed 3 iterations of simulated active learning and repeated the entire procedure 5 times. To simulate active learning, the entire dataset of 4,022 variable-length protein sequences, designed as antibodies for an anonymized target antigen A, was split into 5 groups of sizes 1230, 736, 746, and 600. The first group served as the initial training set for the one or more property computation models 310 while the next three groups served as the "candidate pools" from which 200 molecule designs were selected during each iteration. The final remaining group served as a held-out test set. As shown in Panel (A) of FIGS. 10A-B, qNEHVI-DAG once again outperforms qNEHVI and Random in the number of joint positives. The log posterior density evaluated at the affinity measurements for the joint positives (expressing binders) in the test set shown in Panel (B) of FIGS. 10A-B is also highest for qNEHVI-DAG, which indicates that the property computation models 310 from qNEHVI-DAG had the most accurate beliefs about the joint positives after the final iteration.

In view of the above-described implementations of subject matter this application discloses the following list of examples, wherein one feature of an example in isolation or more than one feature of said example taken in combination and, optionally, in combination with one or more features of one or more further examples are further examples also falling within the disclosure of this application:

Item 1: A computer-implemented method, comprising: applying, to a first molecule design, one or more property computational models trained to determine a first probability of the first molecule design exhibiting a first property and second probability of the first molecule design exhibiting a second property; determining, based at least on an output of the one or more property computational models, a first plurality of samples associated with the first molecule design, each sample of the first plurality of samples including a first value of the first property exhibited by the first molecule design and a second value of the second property exhibited by the first molecule design having the first value for the first property; identifying, within the first plurality of samples, a first set of samples in which the first value of the first property satisfies a first criterion; determining, based at least on the first set of samples, a first utility metric corresponding to a first expected improvement in the first property and the second property of the first molecule design over the first property and the second property of one or more baseline molecule designs; and identifying, based at least on the first utility metric of the first molecule design, the first molecule design as a candidate for synthesis.

Item 2: The method of Item 1, wherein the first utility metric is determined by applying an expected hypervolume improvement (EHVI), a noisy expected hypervolume improvement (NEHVI), a Pareto efficient global optimization (ParEGO), a max-value entropy search method (MESMO), or a joint entropy search (JES).

Item 3: The method of any of Items 1 to 2, wherein the first property and the second property of the one or more baseline molecules are determined based on one or more in vitro measurements and/or in vivo characterizations associated with the one or more baseline molecule designs.

Item 4: The method of any of Items 1 to 3, further comprising: retraining, based at least on one or more in vitro measurements and/or in vivo characterizations associated with the one or more baseline molecule designs, the one or more property computational models; and applying the one or more retrained property computational models to determine the first property and the second property of the one or more baseline molecules.

Item 5: The method of any of Items 1 to 4, further comprising: identifying, within the first plurality of samples, a second set of samples in which the first value of the first property fails to satisfy the first criterion.

Item 6: The method of Item 5, wherein the first utility metric is determined to include a first contribution from the first set of samples and exclude a second contribution from the second set of samples.

Item 7: The method of any of Items 1 to 6, further comprising: applying, to the first molecule design, the one or more property computational models trained to determine a third probability of the first molecule design exhibiting a third property; determining, based at least on the output of the one or more property computational models, the first plurality of samples to further include, as a part of each sample, a third value of the third property exhibited by the first molecule design; identifying the first set of samples further based on the first value of the first property satisfying the first criterion and the second value of the second property satisfying a second criterion; and determining, based at least on the first set of samples, the first utility metric to further correspond to the first expected improvement in the first property, the second property, and the third property of the first molecule design over the first property, the second property, and the third property of the one or more baseline molecules.

Item 8: The method of Item 7, wherein the first property and the second property occupy a same level a hierarchy above the third property such that the first molecule design is required to satisfy the first criterion associated with the first property as well as the second criterion associated with the second property before the first molecule design is evaluated for the third property.

Item 9: The method of Item 7, wherein the first property and the second property occupy different levels of a hierarchy above the third property such that the first molecule design is required to satisfy the first criterion associated with the first property before the first molecule design is evaluated for the second property, and wherein the first molecule design is further required to satisfy the second criterion associated the second property before the first molecule design is evaluated for the third property.

Item 10: The method of any of Items 7 to 9, wherein each of the first property, the second property, and the third property is a different one of expression, binding affinity, specificity, and thermostability.

Item 11: The method of Item 1, wherein the one or more property computational models includes a first property computational model trained to determine the first probability of the first molecule design exhibiting the first property.

Item 12: The method of Item 11, wherein the first property computational model includes a first probabilistic binary classifier trained to determine the first probability of the first molecule exhibiting the first property, and wherein the first binary classifier outputs a first value when the first probability satisfies a second threshold and a second value when the first probability fails to satisfy the second threshold.

Item 13: The method of any of Items 11 to 12, wherein the first property computational model includes a first probabilistic regressor trained to determine the first value of the first property exhibited by the first molecule design.

Item 14: The method of any of Items 11 to 13, wherein the one or more property computational models further includes a second property computational model trained to determine the second probability of the first molecule exhibiting the second property.

Item 15: The method of Item 14, wherein the second property computational model includes a second binary classifier trained to determine the second probability of the first molecule exhibiting the second property, and wherein the second binary classifier outputs a first value when the second probability satisfies a second threshold and a second value when the second probability fails to satisfy the second threshold.

Item 16: The method of any of Items 14 to 15, wherein the second property computational model includes a second regressor trained to determine the second value of the second property exhibited by the first molecule design.

Item 17: The method of any of Items 1 to 16, wherein the one or more property computational models include an ensemble of property computational models, and wherein the first probability of the first molecule design exhibiting the first property and/or the second probability of the first molecule design exhibiting the second property are determined based at least on an output of the ensemble of property computational models.

Item 18: The method of any of Items 1 to 17, further comprising: applying, to a second molecule design, the one or more property computational to determine a third probability of the second molecule design exhibiting the first property and a fourth probability of the second molecule design exhibiting the second property; determining, based at least on the output of the one or more property computational models, a second plurality of samples associated with the second molecule design, each sample of the second plurality of samples including a third value of the first property exhibited by the second molecule design and a fourth value of the second property exhibited the second molecule design; identifying, within the second plurality of samples, a second set of samples in which the third value of the first property satisfies the first criterion; determining, based at least on the second set of samples, a second utility metric corresponding to a second expected improvement in the first property and the second property of the second molecule design over the first property and the second property of the one or more baseline molecule designs; and identifying, based at least on the second utility metric of the second molecule design, the second molecule design as another candidate for synthesis.

Item 19: The method of Item 18, wherein the one or more baseline molecule designs are updated to include the first molecule design such that the second expected improvement includes an expected improvement in the first property and the second property of the second molecule design over the first property and the second property of the first molecule design.

Item 20: The method of Item 19, wherein the one or more baseline molecule designs are updated to include one or more in vivo measurements and/or in vivo characterizations of the first property and/or the second property exhibited by the first molecule design.

Item 21: The method of any of Items 19 to 20, wherein the one or more baseline molecule designs are updated to include an average of the first plurality of samples associated with the first molecule design.

Item 22: The method of any of Items 18 to 21, wherein the second utility metric is determined to include a first contribution from the second set of samples and exclude a second contribution from a third set of samples in which the third value of the first property fails to satisfy the first criterion.

Item 23: The method of any of Items 18 to 22, wherein the first molecule design and the second molecule design are further identified as candidates for batch in vitro and/or in vivo assessment.

Item 24: The method of any of Items 1 to 23, wherein each of the first probability of the first molecule design exhibiting the first property and/or the second probability of the first molecule design exhibiting the second property includes (i) a first probability distribution across a first value indicative of a corresponding property being present in the first molecule design and a second value indicative of the corresponding property being absent from the first molecule design, and (ii) a second probability distribution across a range of possible values indicative of a magnitude of the corresponding property exhibited by the first molecule design.

Item 25: The method of any of Items 1 to 24, wherein the first molecule design is identified as the candidate for synthesis based at least on the first utility metric of the first molecule design satisfying one or more thresholds.

Item 26: The method of any of Items 1 to 25, further comprising: selecting an N quantity of molecule designs having a highest utility metric as candidates for synthesis, the first molecule design being identified as the candidate for synthesis based at least on the first molecule design being one of the N quantity of molecule designs having the highest utility metric.

Item 27: The method of any of Items 1 to 26, wherein the first value of the first property satisfies the first criterion by satisfying a threshold, falling within one or more intervals of values, or being a member of a set.

Item 28: The method of any of Items 1 to 27, further comprising: identifying, based at least on a presence or an absence of one or more specific amino acid residues in the first molecule design, the first molecule design as the candidate for synthesis.

Item 29: The method of any of Items 1 to 28, wherein the first plurality of samples comprises a distribution of the second value of the second property exhibited by the first molecule design across the first value of the first property exhibited by the first molecule design.

Item 30: The method of any of Items 1 to 29, wherein the first molecule design is a protein molecule, a small molecule, an ion, a nucleic acid, a polysaccharide, and/or a glycolipid.

Item 31: The method of any of Items 1 to 30, further comprising: applying a molecule design computational model to generate the first molecule design.

Item 32: A system, comprising: at least one data processor; and at least one memory storing instructions, which when executed by the at least one data processor, result in operations comprising the method of any of Items 1 to 31.

Item 33: A non-transitory computer readable medium storing instructions, which when executed by at least one data processor, result in operations comprising the method of any of Items 1 to 31.

Figure 11:
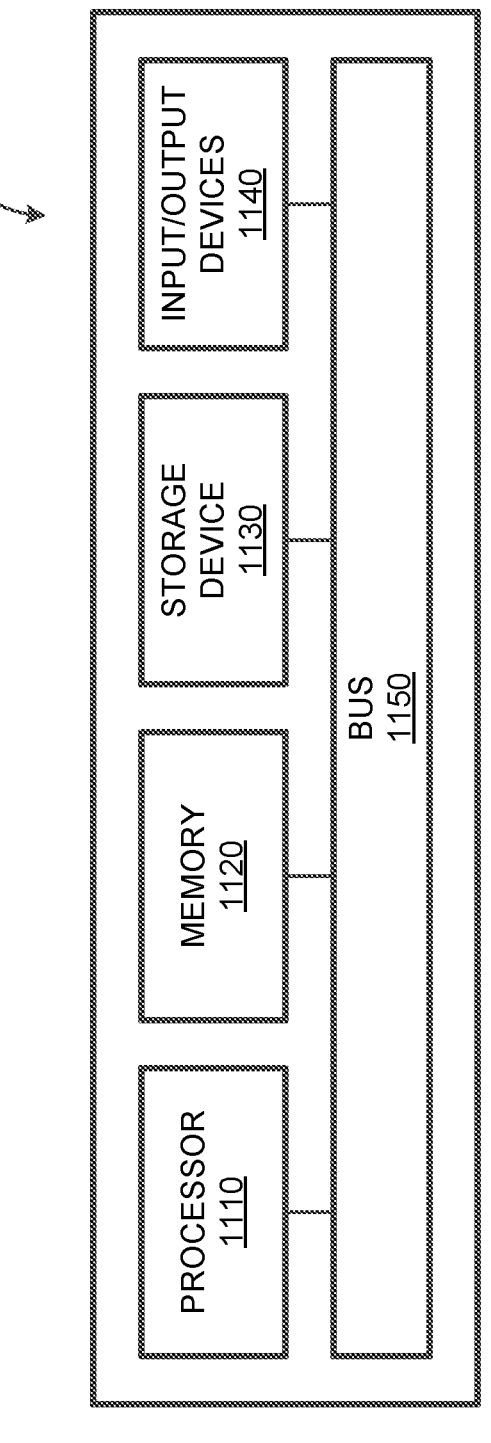
FIG. 11 depicts a block diagram illustrating an example of a computing system, in accordance with some example embodiments.

FIG. 11 depicts a block diagram illustrating an example of a computing system 1100, in accordance with some example embodiments. Referring to FIGS. 1-11, the computing system 1100 may be used to implement the molecule design engine 110, the selection engine 120, the laboratory equipment 130, the client device 140, and/or any components therein.

As shown in FIG. 11, the computing system 1100 can include a processor 1110, a memory 1120, a storage device 1130, and input/output devices 1140. The processor 1110, the memory 1120, the storage device 1130, and the input/output devices 1140 can be interconnected via a system bus 1150. The processor 1110 is capable of processing instructions for execution within the computing system 1100. Such executed instructions can implement one or more components of, for example, the molecule design engine 110, the selection engine 120, the laboratory equipment 130, the client device 140, and/or the like. In some example embodiments, the processor 1110 can be a single-threaded processor. Alternately, the processor 1110 can be a multi-threaded processor. The processor 1110 is capable of processing instructions stored in the memory 1120 and/or on the storage device 1130 to display graphical information for a user interface provided via the input/output device 1140.

The memory 1120 is a computer readable medium such as volatile or non-volatile that stores information within the computing system 1100. The memory 1120 can store data structures representing configuration object databases, for example. The storage device 1130 is capable of providing persistent storage for the computing system 1100. The storage device 1130 can be a floppy disk device, a hard disk device, an optical disk device, or a tape device, or other suitable persistent storage means. The input/output device 1140 provides input/output operations for the computing system 1100. In some example embodiments, the input/output device 1140 includes a keyboard and/or pointing device. In various implementations, the input/output device 1140 includes a display unit for displaying graphical user interfaces.

According to some example embodiments, the input/output device 1140 can provide input/output operations for a network device. For example, the input/output device 1140 can include Ethernet ports or other networking ports to communicate with one or more wired and/or wireless networks (e.g., a local area network (LAN), a wide area network (WAN), the Internet).

In some example embodiments, the computing system 1100 can be used to execute various interactive computer software applications that can be used for organization, analysis and/or storage of data in various formats. Alternatively, the computing system 1100 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1140. The user interface can be generated and presented to a user by the computing system 1100 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

The invention claimed is:

1. A computer-implemented method, comprising:

applying, to a molecule design, one or more property computational models to determine a probability of the molecule design exhibiting a first property and a probability of the molecule design exhibiting a second property;

determining, based at least on the probability of the molecule design exhibiting the first property and probability of the molecule design exhibiting the second property, a plurality of samples associated with the molecule design, where each sample of the plurality of samples includes a value of the first property exhibited by the molecule design and a value of the second property exhibited by the molecule design;

identifying, within the plurality of samples associated with the molecule design, a set of samples in which the value of the first property of the molecule design satisfies a criterion;

identifying, within the plurality of samples associated with the molecule design, a set of samples in which the value of the first property of the molecule design fails to satisfy the criterion;

determining, based at least on the set of samples in which the value of the first property of the molecule design satisfies the criterion and the set of samples in which the value of the first property of the molecule design fails to satisfy the criterion, a utility metric corresponding to an expected improvement in the first property and the second property of the molecule design over the first property and the second property of a baseline molecule design, where the determining the utility metric includes prioritizing the first property over the second property, and where the prioritizing includes the set of samples in which the value of the first property of the molecule design fails to satisfy the criterion having a reduced contribution to the utility metric regardless of a corresponding value of the second property of the molecule design; and determining that the utility metric of the molecule design indicates that the first property and the second property of the molecule design improves upon the first property and the second property of the baseline molecule design;

in response to the utility metric of the molecule design indicating that the first property and the second property of the molecule design improves upon the first property and the second property of the baseline molecule design, identifying the molecule design as a candidate for synthesis; and synthesizing one or more molecules identified as candidates for synthesis.

2. The method of claim 1, wherein the utility metric is determined by applying an expected hypervolume improvement (EHVI), a noisy expected hypervolume improvement (NEHVI), a Pareto efficient global optimization (ParEGO), a max-value entropy search method (MESMO), or a joint entropy search (JES).

3. The method of claim 1, further comprising:

retraining, based at least on one or more in vitro measurements and/or in vivo characterizations associated with the baseline molecule design and/or the one or more synthesized molecules, the one or more property computational models; and applying the one or more retrained property computational models to determine the first property and the second property of the baseline molecule design.

4. The method of claim 3, wherein the operations further comprise:

applying the one or more retrained property computational models to determine the first property and the second property of the molecule design; and determining, based at least on an output of the one or more retrained property computational models, the utility metric of the molecule design.

5. The method of claim 3, wherein the operations further comprise:

applying the one or more retrained property computational models to determine the first property and the second property of one or more subsequent molecule designs.

6. The method of claim 1, further comprising:

identifying, within the plurality of samples, a set of samples in which the value of the first property fails to satisfy the criterion; and determining the utility metric to include a contribution from the set of samples in which the value of the first property satisfies the criterion and exclude a contribution from the set of samples in which the value of the first property fails to satisfy the criterion.

7. The method of claim 1, further comprising:

applying, to the molecule design, the one or more property computational models trained to determine a probability of the molecule design exhibiting a third property;

determining, based at least on the output of the one or more property computational models, the plurality of samples to further include, as a part of each sample, a value of the third property exhibited by the molecule design;

identifying the set of samples further based on the value of the first property satisfying the criterion and the value of the second property satisfying an additional criterion; and determining, based at least on the set of samples, the utility metric to further correspond to an expected improvement in the first property, the second property, and the third property of the molecule design over the first property, the second property, and the third property of the baseline molecule design.

8. The method of claim 7, wherein the first property and the second property occupy a same level a hierarchy such that the molecule design is required to satisfy the criterion associated with the first property as well as the additional criterion associated with the second property before the molecule design is evaluated for the third property.

9. The method of claim 7, wherein the first property and the second property occupy different levels of a hierarchy such that the molecule design is required to satisfy the criterion associated with the first property before the molecule design is evaluated for the second property, and wherein the molecule design is further required to satisfy the additional criterion associated the second property before the molecule design is evaluated for the third property.

10. The method of claim 1, wherein the one or more property computational models includes a first property computational model trained to determine the probability of the molecule design exhibiting the first property or wherein the one or more property computational models includes a second property computational model trained to determine the probability of the molecule exhibiting the second property.

11. The method of claim 10, wherein the first property computational model or the second property computational model includes a probabilistic binary classifier and/or a probabilistic regressor.

12. The method of claim 1, wherein the one or more property computational models include an ensemble of property computational models, and wherein the probability of the molecule design exhibiting the first property and/or the probability of the molecule design exhibiting the second property are determined based at least on an output of each property computational model comprising the ensemble of property computational models.

13. The method of claim 1, further comprising:

applying, to a different molecule design, the one or more property computational to determine a probability of the different molecule design exhibiting the first property and a probability of the different molecule design exhibiting the second property;

determining, based at least on the probability of the different molecule design exhibiting the first property and the probability of the different molecule design exhibiting the second property, a plurality of samples associated with the different molecule design, each sample of the plurality of samples including a value of the first property exhibited by the different molecule design and a value of the second property exhibited by the different molecule design;

identifying, within the plurality of samples associated with the different molecule design, a set of samples in which the value of the first property of the different molecule design satisfies the criterion;

identifying, within the plurality of samples associated with the different molecule design, a set of samples in which the value of the first property of the different molecule design fails to satisfy the criterion;

determining, based at least on the set of samples in which the value of the first property of the different molecule design satisfies the criterion and the set of samples in which the value of the first property of the different molecule design fails to satisfy the criterion, a utility metric corresponding to an expected improvement in the first property and the second property of the different molecule design over the first property and the second property of the baseline molecule design; and identifying, based at least on the utility metric of the different molecule design, the different molecule design as an additional candidate for synthesis.

14. The method of claim 13, wherein the molecule design becomes an additional baseline molecule design such that the expected improvement of the different molecule design includes an expected improvement in the first property and the second property of the different molecule design over the first property and the second property of the molecule design.

15. The method of claim 14, wherein the additional baseline molecule design is updated to include one or more in vivo measurements and/or in vivo characterizations of the first property and/or the second property exhibited by the molecule design.

16. The method of claim 14, wherein the additional baseline molecule design is updated to include an average of the plurality of samples associated with the molecule design.

17. The method of claim 1, wherein the probability of the molecule design exhibiting the first property and/or the probability of the molecule design exhibiting the second property include (i) a probability distribution across a value indicative of a corresponding property being present in the molecule design and a value indicative of the corresponding property being absent from the molecule design, and (ii) a probability distribution across a range of possible values indicative of a magnitude of the corresponding property exhibited by the molecule design.

18. The method of claim 1, wherein the molecule design is identified as the candidate for synthesis based at least on the utility metric of the molecule design satisfying one or more thresholds.

19. The method of claim 1, further comprising:

selecting a subset of molecule designs from a plurality of molecule designs for synthesis, where the subset of molecule designs includes an N quantity of molecule designs having a highest utility metric amongst the plurality of molecule designs.

20. The method of claim 1, further comprising:

identifying, based at least on a presence or an absence of one or more specific amino acid residues in the molecule design, the molecule design as the candidate for synthesis.

21. The method of claim 1, wherein the plurality of samples comprises a distribution of the value of the second property exhibited by the molecule design across the value of the first property exhibited by the molecule design.

22. The method of claim 1, wherein the value of the first property satisfies the criterion by satisfying a threshold, falling within one or more intervals of values, or being a member of a set.

23. The method of claim 1, wherein the molecule design comprises at least a portion of a protein molecule, a small molecule, an ion, a nucleic acid, a polysaccharide, and/or a glycolipid.

24. The method of claim 1, wherein the first property comprises expression and the second property comprises binding affinity.

25. The method of claim 1, wherein the first property comprises binding affinity and the second property comprises a developability property.

26. The method of claim 1, wherein the operations further comprise:

identifying, based at least on the utility metric of the molecule design, the molecule design as a joint positive design in which improving the value of the first property worsens the value of the second property; and identifying, based at least on the molecule design being the joint positive design, the molecule design as a candidate for synthesis.

\*　\*　\*　\*　\*